United States Patent
Nettekoven et al.

(10) Patent No.: US 7,388,095 B2
(45) Date of Patent: Jun. 17, 2008

(54) 5-SUBSTITUTED INDOLE-2-CARBOXAMIDE DERIVATIVES

(75) Inventors: Matthias Nettekoven, Grenzach-Wyhlen (DE); Jean-Marc Plancher, Hagenthal-le-Bas (FR); Hans Richter, Grenzach-Wyhlen (DE); Olivier Roche, Folgensbourg (FR); Sven Taylor, Riedisheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/604,563

(22) Filed: Nov. 27, 2006

(65) Prior Publication Data

US 2007/0123525 A1     May 31, 2007

(30) Foreign Application Priority Data

Nov. 30, 2005   (EP)  ................... 05111477

(51) Int. Cl.
    *C07D 417/14*    (2006.01)
    *C07D 413/14*    (2006.01)
    *C07D 401/14*    (2006.01)
(52) U.S. Cl. .......................... 544/55; 544/62; 544/111; 546/187; 546/201; 546/277.4
(58) Field of Classification Search ................. 544/111
See application file for complete search history.

(56) References Cited

U.S. PATENT DOCUMENTS

| | | | |
|---|---|---|---|
| 4,183,857 A | 1/1980 | Kollmeyer | |
| 4,598,089 A | 7/1986 | Hadvary et al. | |
| 4,931,463 A | 6/1990 | Barbier et al. | |
| 4,983,746 A | 1/1991 | Barbier et al. | |
| 5,175,186 A | 12/1992 | Barbier et al. | |
| 5,246,960 A | 9/1993 | Barbier et al. | |
| 5,399,720 A | 3/1995 | Karpf et al. | |
| 6,004,996 A | 12/1999 | Shah et al. | |
| 2004/0224952 A1 | 11/2004 | Cowart et al. | |

FOREIGN PATENT DOCUMENTS

| | | |
|---|---|---|
| EP | 0 189 577 | 12/1989 |
| EP | 0 185 359 | 12/1991 |
| EP | 0 524 495 | 10/1996 |
| EP | 0 443 449 | 5/1997 |
| WO | WO 99/34786 | 7/1999 |
| WO | WO 00/09122 | 2/2000 |
| WO | WO 00/09123 | 2/2000 |
| WO | WO 00/58293 | 10/2000 |
| WO | WO 01/74773 A2 | 10/2001 |
| WO | WO 02/072548 A2 | 9/2002 |
| WO | WO 2004/000831 A1 | 12/2003 |
| WO | WO 2005012249 A2 | 2/2005 |
| WO | WO 2005/123716 A1 | 12/2005 |

OTHER PUBLICATIONS

Arnaiz, et al. Bioorganic & Medicinal Chemistry Letters. 10 (2000), 957-961.*
Burks 1994 in Johnson L.R. ed., Physiology of the Gastrointestinal Tract, Raven Press, NY, pp. 211-242.
Leurs et al., Br J. Pharmacol. 1991, 102, pp. 179-185.
Raithel et al., Int. Arch. Allergy Immunol. 1995, 108, 127-133.
Panula et al., Proc. Natl. Acad. Sci. USA 1984, 81, 2572-2576.
Inagaki et al., J. Comp. Neurol 1988, 273, 283-300.
Arrang et al., Nature 1983, 302, 832-837.
Arrang et al., Neuroscience 1987, 23, 149-157.
Clapham & Kilpatrik, Br. J. Pharmacol. 1982, 107, 919-923.
Blandina et al. in The Histamine H3 Receptor (Leurs RL and Timmermann H eds, 1998, pp. 27-40, Elsevier, Amsterdam, The Netherlands).
Masaki et al; Endocrinol. 2003, 144, 2741-2748.
Hancock et al., European J. of Pharmacol. 2004, 487, 183-197.
Timmermann, J. Med. Chem. 1990, 33, 4-11.
Mederski, W. W. K. R.; Lefort, M.; Germann, M. Kux, D. Tetrahedron 1999 55 12757.
Watanabe, M; Nishiyama, M.; Yamamoto, T.; Koie, Y, Tetrahedron Letters 2000, 41, 481.
Old, D. W.; Harris, M. C.; Buchwald, S. L 2000 2 10 1403.
Klapars, A.; Antilla, J. C.; Huang, X.; Buchwald, S. L. J. Am. Chem. Soc. 2001 123 7727.
Zaragoza, F., Stephensen, H., Knudsen, S. M., Pridal, L., Wulff, B. S., Rimvall, K. Journal of Medicinal Chemistry 2004, 47, 2833.

(Continued)

*Primary Examiner*—Joseph McKane
*Assistant Examiner*—Shawquia Young
(74) *Attorney, Agent, or Firm*—George W. Johnston; Dennis P. Tramaloni; Brian C. Remy

(57) ABSTRACT

The present invention relates to compounds of formula I

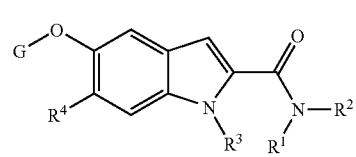

wherein $R^1$ to $R^4$ and G are as defined in the description and claims and pharmaceutically acceptable salts thereof. The compounds are useful for the treatment and/or prevention of diseases which are associated with the modulation of H3 receptors.

19 Claims, No Drawings

OTHER PUBLICATIONS

A. F. Abdel-Magid, K. G. Carson, B. D. Harris, C. A. Maryanoff and R. K. Shah, Journal of Organic Chemistry, 1996, 61, 3849.
CAS Registry No. 841302-37-2, Oct. 16, 2006.
CAS Registry No. 27202-71-7, Oct. 16, 2006.
Takahashi, K, Tokita, S., Kotani, H. (2003) J. Pharmacol. Exp. Therapeutics 307, 213-218.
Bettoni et al, Gaz. Chim. Ital. 1972 102 189).

* cited by examiner

5-SUBSTITUTED INDOLE-2-CARBOXAMIDE DERIVATIVES

PRIORITY TO RELATED APPLICATIONS

This application claims the benefit of European Application No. 05111477.5, filed Nov. 30, 2005, which is hereby incorporated by reference in its entirety.

FIELD OF THE INVENTION

The present invention is concerned with novel 5-substituted indole-2-carboxamide derivatives, their manufacture, pharmaceutical compositions containing them and their use as medicaments. The active compounds of the present invention are useful in treating obesity and other disorders.

In particular, the present invention relates to compounds of the general formula

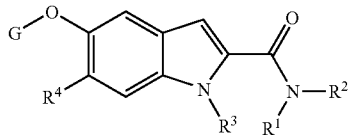

I and pharmaceutically acceptable salts thereof.

The compounds of formula I are antagonists and/or inverse agonists at the histamine 3 receptor (H3 receptor).

All documents cited or relied upon below are expressly incorporated herein by reference.

BACKGROUND

Histamine (2-(4-imidazolyl) ethylamine) is one of the aminergic neurotransmitters which is widely distributed throughout the body, e.g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tuberomammillary nucleus of the posterior basal hypothalamus. From there, the cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the central nervous system (CNS) and the periphery through four distinct histamine receptors, the histamine H1, H2, H3 and H4 receptors.

H3 receptors are predominantly localized in the CNS. As an autoreceptor, H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

A need therefore exist to provide selective, directly acting H3 receptor antagonists respectively inverse agonists. Such antagonists/inverse agonists are useful as therapeutically active substances, particularly in the treatment and/or prevention of diseases which are associated with the modulation of H3 receptors.

SUMMARY OF THE INVENTION

In an embodiment of the present invention, a compound of formula (I):

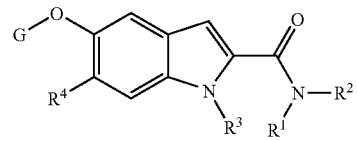

I wherein:
R¹ is selected from the group consisting of
  lower alkyl, lower alkenyl, lower alkynyl,
  cycloalkyl, lower cycloalkylalkyl,
  lower hydroxyalkyl,
  lower alkoxyalkyl,
  lower alkylsulfanylalkyl,
  lower dialkylaminoalkyl,
  lower dialkylcarbamoylalkyl,
  phenyl unsubstituted or substituted with one or two groups independently selected from lower alkyl, lower halogenoalkoxy and lower hydroxyalkyl,
  lower phenylalkyl wherein the phenyl ring may be unsubstituted or substituted with one or two groups independently selected from lower alkyl, halogen, lower alkoxy and lower hydroxyalkyl, lower heteroarylalkyl wherein the heteroaryl ring may be unsubstituted or substituted with one or two groups independently selected from lower alkyl, halogen, lower alkoxy and lower hydroxyalkyl and lower heterocyclylalkyl wherein the heterocyclyl ring may be unsubstituted or substituted with one or two lower alkyl groups;

$R^2$ is selected from the group consisting of hydrogen lower alkyl, lower alkenyl, lower alkynyl, cycloalkyl, lower cycloalkylalkyl, lower hydroxyalkyl, lower alkoxyalkyl, lower alkylsulfanylalkyl, lower dialkylaminoalkyl, lower dialkylcarbamoylalkyl, phenyl unsubstituted or substituted with one or two groups independently selected from lower alkyl, lower halogenoalkoxy and lower hydroxyalkyl, lower phenylalkyl wherein the phenyl ring may be unsubstituted or substituted with one or two groups independently selected from lower alkyl, halogen, lower alkoxy and lower hydroxyalkyl, lower heteroarylalcyl wherein the heteroaryl ring may be unsubstituted or substituted with one or two groups independently selected from lower alkyl, halogen, lower alkoxy and lower hydroxyalkyl and lower heterocyclylalkyl wherein the heterocycly ring may be unsubstituted or substituted with one or two lower alkyl groups; or $R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulphur, a sulfinyl group or a sulfonyl group, said saturated or partly unsaturated heterocyclic ring being unsubstituted or substituted by one, two or three groups independently selected from lower alkyl, halogen, halogenoalkyl, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen;

$R^3$ is selected from the group consisting of hydrogen, lower alkyl, lower hydroxyalkyl, lower alkoxyalkyl, lower halogenoalkyl, lower cycloalkylalkyl, lower alkanoyl, lower cyanoalkyl, lower alkylsulfonyl, phenylsulfonyl wherein the phenyl ring may be unsubstituted or substituted with one or two groups independently selected from lower alkyl, halogen, lower alkoxy lower halogenoalkoxy and lower hydroxyalkyl;

phenyl unsubstituted or substituted with one or two groups independently selected from lower alkyl, halogen, lower alkoxy, lower halogenoalkoxy and lower hydroxyalkyl; lower phenylalkyl, wherein the phenyl ring may be unsubstituted or substituted with one or two groups independently selected from lower alkyl, halogen, lower alkoxy, lower halogenoalkoxy and lower hydroxyalkyl; and heteroaryl unsubstituted or substituted with one or two groups independently selected from lower alkyl or halogen;

$R^4$ is hydrogen or halogen;

G is a group selected from

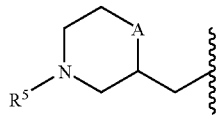

G1

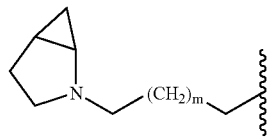

G2

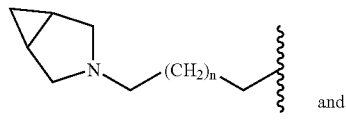

G3 and

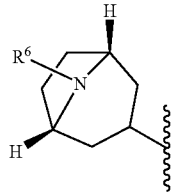

G4 wherein $R^5$ is selected from lower alkyl, cycloalkyl, lower cycloalkylalkyl and lower phenylalkyl;

A is selected from $CH_2$, O and S;

m is 0, 1 or 2;

n is 0, 1 or 2;

$R^6$ is lower alkyl or cycloalkyl;

and pharmaceutically acceptable salts thereof.

In another embodiment of the present invention, provided is a process for the manufacture of a compound according to formula I, comprising the steps of:

reacting a compound of the formula II

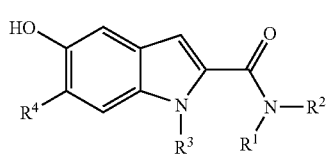

II wherein $R^1$ to $R^4$ are as defined herein before, with an alcohol of the formula III

HO-G    III wherein G is as defined herein before, in the presence of a trialkylphosphine or triphenylphosphine and of an azo compound to obtain a compound of the formula I

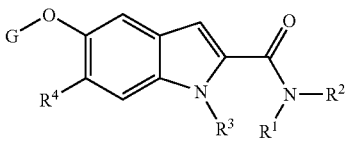

wherein $R^1$ to $R^4$ and G are as defined herein before, and if desired, converting the compound obtained into a pharmaceutically acceptable acid addition salt.

In a further embodiment of the present invention, provided is a pharmaceutical composition, comprising a therapeutically effective amount of a compound according to formula I as well as a pharmaceutically acceptable carrier and/or adjuvant.

In a yet another embodiment of the present invention, provided is a method for the treatment and/or prevention of diseases which are associated with the modulation of H3 receptors, comprising the step of administering a therapeutically active amount of a compound according to formula I to a human being or animal in need thereof.

In a still further embodiment of the present invention, provided is a method for the treatment or prevention of obesity in a human being or animal, comprising the step of administering a therapeutically effective amount of a compound of formula I in combination or association with a therapeutically effective amount of a compound selected from the group consisting of a lipase inhibitor, an anorectic agent, a selective serotonin reuptake inhibitor and an agent that stimulates metabolism of body fat, to said human being or animal in need thereof.

In a yet still another embodiment of the present invention, provided is a method of treatment or prevention of type II diabetes in a human being or animal, comprising the step of administering a therapeutically effective amount of a compound of formula I in combination or association with a therapeutically effective amount of an anti-diabetic agent to said human being or animal in need thereof.

DETAILED DESCRIPTION

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_8$-alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "lower alkenyl" or "$C_{2-8}$-alkenyl", alone or in combination, signifies a straight-chain or branched hydrocarbon radical comprising an olefinic bond and up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "lower alkynyl" or "$C_{2-8}$-alkynyl", alone or in combination, signifies a straight-chain or branched hydrocarbon residue comprising a triple bond and up to 8, preferably up to 6, particularly preferred up to 4 carbon atoms. Examples of alkynyl groups are ethinyl, 1-propinyl, or 2-propinyl. A preferred example is 2-propinyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. Especially preferred are cyclopropyl, cyclopentyl and cyclohexyl.

The term "lower cycloalkylalkyl" or "$C_{3-7}$-cycloalkyl-$C_{1-8}$-allyl" refers to lower alkyl groups as defined above wherein at least one of the hydrogen atoms of the lower alkyl group is replaced by cycloalkyl. A preferred example is cyclopropylmethyl.

The term "alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec.butoxy and tert.-butoxy, preferably methoxy and ethoxy and most preferred methoxy.

The term "lower alkoxyalkyl" or "$C_{1-8}$-alkoxy-$C_{1-8}$-alkyl" refers to lower alkyl groups as defined above wherein at least one of the hydrogen atoms of the lower alkyl groups is replaced by an alkoxy group, preferably methoxy or ethoxy. Among the preferred lower alkoxyalkyl groups are 2-methoxyethyl or 3-methoxypropyl.

The term "alkylsulfanyl" or "$C_{1-8}$-alkylsulfanyl" refers to the group R'—S—, wherein R' is lower alkyl and the term "lower alkyl" has the previously given significance. Examples of alkylsulfanyl groups are e.g. methylsulfanyl or ethylsulfanyl.

The term "lower alkylsulfanylalkyl" or "$C_{1-8}$-alkylsulfanyl-$C_{1-8}$-alkyl" refers to lower alkyl groups as defined above wherein at least one of the hydrogen atoms of the lower alkyl groups is replaced by an alkylsulfanyl group, preferably methylsulfanyl. An example for a preferred lower alkylsulfanylalkyl group is 2-methylsulfanylethyl.

The term "alkylsulfonyl" or "lower alkylsulfonyl" refers to the group R'—S(O)$_2$—, wherein R' is lower alkyl and the term "lower alkyl" has the previously given significance. Examples of alkylsulfonyl groups are e.g. methylsulfonyl or ethylsulfonyl.

The term "halogen" refers to fluorine, chlorine, bromine and iodine, with fluorine, chlorine and bromine being preferred.

The term "lower halogenoalkyl" or "halogen-$C_{1-8}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, fluoromethyl and chloromethyl, with trifluoromethyl being especially preferred.

The term "lower halogenoalkoxy" or "halogen-$C_{1-8}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluormethoxy and chloromethoxy, with trifluoromethoxy being especially preferred.

The term "lower hydroxyalkyl" or "hydroxy-$C_{1-8}$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl.

The term "dialkylamino" refers to the group —NR'R", wherein R' and R" are lower alkyl and the term "lower alkyl" has the previously given significance. A preferred dialkylamino group is dimethylamino.

The term "lower dialkylaminoalkyl" or "$C_{1-8}$-dialkylamino-$C_{1-8}$-alkyl" refers to lower alkyl groups as defined above wherein at least one of the hydrogen atoms of the lower alkyl group is replaced by a dialkylamino group, preferably dimethylamino. A preferred lower dialkylaminoalkyl group is 3-dimethylaminopropyl.

The term "lower alkanoyl" refers to the group —CO—R', wherein R' is lower alkyl and the term "lower alkyl" has the previously given significance. Preferred is a group —CO—R', wherein R' is methyl, meaning an acetyl group.

The term "carbamoyl" refers to the group —CO—$NH_2$.

The term "dialkylcarbamoyl" or "$C_{1-8}$-dialkylcarbamoyl" refers to the group —CO—NR'R" wherein R' and R" are lower alkyl and the term "lower alkyl" has the previously given significance. A preferred dialkylcarbamoyl group is dimethylcarbamoyl.

The term "lower dialkylcarbamoylalkyl" or "$C_{1-8}$-dialkylcarbamoyl-$C_{1-8}$-alkyl" refers to lower alkyl groups as defined above wherein at least one of the hydrogen atoms of the lower alkyl group is replaced by a dialkylcarbamoyl group as defined herein before. A preferred lower dialkylcarbamoylalkyl groups is dimethylcarbamoylmethyl.

The term "lower phenylalkyl" or "phenyl-$C_{1-8}$-alkyl" to lower alkyl groups as defined above wherein at least one of the hydrogen atoms of the lower alkyl group is replaced by a phenyl group. Preferred lower phenylalkyl groups are benzyl or phenethyl.

The term "heteroaryl" refers to an aromatic 5- or 6-membered ring which can comprise one, two or three atoms selected from nitrogen, oxygen and/or sulphur. Examples of heteroaryl groups are e.g. furyl, pyridyl, pyrazinyl, pyrimidinyl, pyridazinyl, thienyl, isoxazolyl, thiazolyl, isothiazolyl, oxazolyl, imidazolyl, or pyrrolyl. Especially preferred are furyl and pyridyl.

The term "lower heteroarylalkyl" or "heteroaryl-$C_{1-8}$-alkyl" refers to lower alkyl groups as defined above wherein at least one of the hydrogen atoms of the lower alkyl group is replaced by a heteroaryl group as defined above.

The term "heterocyclyl" refers to a saturated or partly unsaturated 5- or 6-membered ring which can comprise one, two or three atoms selected from nitrogen, oxygen and/or sulphur. Examples of heterocyclyl rings include piperidinyl, piperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl and thiomorpholinyl. A preferred heterocyclyl group is piperidinyl.

The term "lower heterocyclylalkyl" or "heterocyclyl-$C_{1-8}$-alkyl" refers to lower alkyl groups as defined above wherein at least one of the hydrogen atoms of the lower alkyl group is replaced by a heterocyclyl group as defined above.

The term "form a 4-, 5-, 6- or 7-membered saturated heterocyclic ring optionally containing a further heteroatom selected from nitrogen, oxygen or sulphur" refers to a saturated N-heterocyclic ring, which may optionally contain a further nitrogen, oxygen or sulphur atom, such as azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, or azepanyl. A "4-, 5-, 6- or 7-membered partly unsaturated heterocyclic ring" means a heterocyclic ring as defined above which contains a double bond, for example 2,5-dihydropyrrolyl or 3,6-dihydro-2H-pyridinyl. A "4-, 5-, 6- or 7-membered saturated or partly unsaturated heterocyclic ring containing a sulfinyl group or a sulfonyl group" means a N-heterocyclic ring that contains a —S(O)— group or a —$SO_2$— group, for example 1-oxothiomorpholinyl or 1,1-dioxothiomorpholinyl. The heterocyclic ring may be unsubstituted or substituted by one, two or three groups independently selected from lower alkyl, lower alkoxy and oxo. The heterocyclic ring may also be condensed with a phenyl ring, said phenyl ring being unsubstituted or substituted by one, two or three groups independently selected from lower alkyl, lower alkoxy and halogen. An example for such a condensed heterocyclic ring is 3,4-dihydro-1H-isoquinoline.

The term "oxo" means that a C-atom of the heterocyclic ring may be substituted by =O, thus meaning that the heterocyclic ring may contain one or more carbonyl (—CO—) groups.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulphuric acid, nitric acid, phosphoric acid and the like, preferably hydrochloric acid and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers" and stereoisomers that are non-superimposable mirror images are termed "enantiomers", or sometimes optical isomers.

A carbon atom bonded to four nonidentical substituents is termed a "chiral center".

In detail, the present invention relates to compounds of the general formula

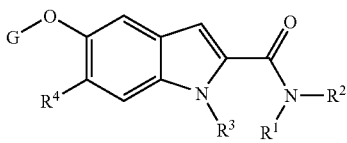

I wherein
$R^1$ is selected from the group consisting of
  lower alkyl, lower alkenyl, lower alkynyl,
  cycloalkyl, lower cycloalkylalkyl,
  lower hydroxyalkyl,
  lower alkoxyalkyl,
  lower alkylsulfanylalkyl,
  lower dialkylaminoalkyl,
  lower dialkylcarbamoylalkyl,
  phenyl unsubstituted or substituted with one or two groups independently selected from lower alkyl, lower halogenoalkoxy and lower hydroxyalkyl,
  lower phenylalkyl wherein the phenyl ring may be unsubstituted or substituted with one or two groups independently selected from lower alkyl, halogen, lower alkoxy and lower hydroxyalkyl,
  lower heteroarylalkyl wherein the heteroaryl ring may be unsubstituted or substituted with one or two groups independently selected from lower alkyl, halogen, lower alkoxy and lower hydroxyalkyl and
  lower heterocyclylalkyl wherein the heterocyclyl ring may be unsubstituted or substituted with one or two lower alkyl groups;
$R^2$ is selected from the group consisting of hydrogen,
  lower alkyl, lower alkenyl, lower alkynyl,
  cycloalkyl, lower cycloalkylalkyl,
  lower hydroxyalkyl, lower alkoxyalkyl,
  lower alkylsulfanylalkyl,
  lower dialkylaminoalkyl,
  lower dialkylcarbamoylalkyl,
  phenyl unsubstituted or substituted with one or two groups independently selected from lower alkyl, lower halogenoalkoxy and lower hydroxyalkyl,
  lower phenylalkyl wherein the phenyl ring may be unsubstituted or substituted with one or two groups independently selected from lower alkyl, halogen, lower alkoxy and lower hydroxyalkyl,
  lower heteroarylalkyl wherein the heteroaryl ring may be unsubstituted or substituted with one or two groups independently selected from lower alkyl, halogen, lower alkoxy and lower hydroxyalkyl and
  lower heterocyclylalkyl wherein the heterocycly ring may be unsubstituted or substituted with one or two lower alkyl groups; or
$R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulphur, a sulfinyl group or a sulfonyl group, said saturated or partly unsaturated heterocyclic ring
  being unsubstituted or substituted by one, two or three groups independently selected from lower alkyl, halogen, halogenoalkyl, hydroxy, lower hydroxyalkyl, lower alkoxy, oxo, phenyl, benzyl, pyridyl and carbamoyl, or
  being condensed with a phenyl ring, said phenyl ring being unsubstituted or substituted by one, two or three groups independently selected from lower alkyl, lower alkoxy and halogen;
$R^3$ is selected from the group consisting of hydrogen, lower alkyl, lower hydroxyalkyl, lower alkoxyalkyl, lower halogenoalkyl, lower cycloalkylalkyl,
  lower alkanoyl, lower cyanoalkyl, lower alkylsulfonyl,
    phenylsulfonyl wherein the phenyl ring may be unsubstituted or substituted with one or two groups independently selected from lower alkyl, halogen, lower alkoxy lower halogenoalkoxy and lower hydroxyalkyl;
    phenyl unsubstituted or substituted with one or two groups independently selected from lower alkyl, halogen, lower alkoxy, lower halogenoalkoxy and lower hydroxyalkyl; lower phenylalkyl, wherein the phenyl ring may be unsubstituted or substituted with one or two groups independently selected from lower alkyl, halogen, lower alkoxy, lower halogenoalkoxy and lower hydroxyalkyl; and
    heteroaryl unsubstituted or substituted with one or two groups independently selected from lower alkyl or halogen;
$R^4$ is hydrogen or halogen;
G is a group selected from

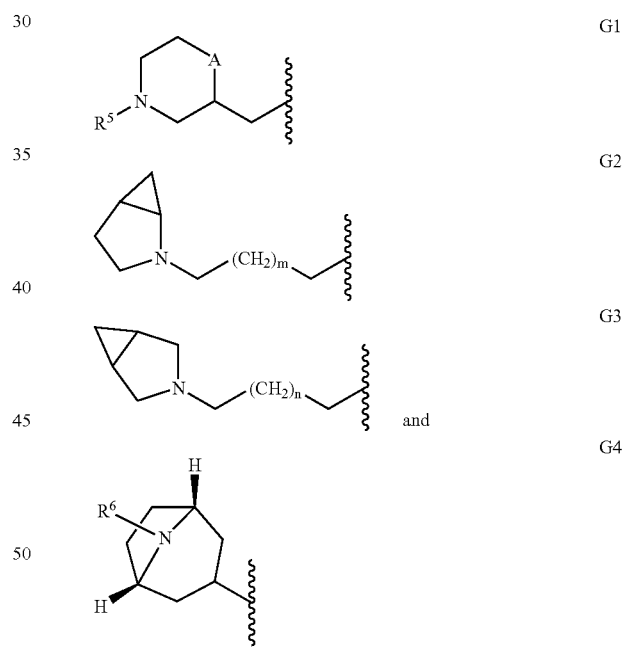

wherein
$R^5$ is selected from lower alkyl, cycloalkyl, lower cycloalkylalkyl and lower phenylalkyl;
A is selected from $CH_2$, O and S;
m is 0, 1 or 2;
n is 0, 1 or 2;
$R^6$ is lower alkyl or cycloalkyl;

and pharmaceutically acceptable salts thereof.

Compounds of formula I according to the present invention are preferred, wherein $R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulphur, a sulfinyl group or a sulfonyl group, said saturated or partly unsaturated heterocyclic ring being unsubstituted or substituted by one, two or three groups independently selected from lower alkyl, halogen, halogenoalkyl, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

More preferred are compounds of formula I according to the invention, wherein $R^1$ and $R^2$ together with the nitrogen atom to which they are attached form a heterocyclic ring selected from the group consisting of morpholine, piperidine, 2,5-dihydropyrrole, pyrrolidine, azepane, piperazine, azetidine, thiomorpholine, 1-oxo-thiomorpholine, 1,1-dioxothiomorpholine and 3,6-dihydro-2H-pyridine, said heterocyclic ring being unsubstituted or substituted by one, two or three groups independently selected from lower alkyl, halogen, halogenoalkyl, hydroxy, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

Even more preferably, $R^1$ and $R^2$ together with the nitrogen atom to which they are attached form a heterocyclic ring selected from the group consisting of morpholine, piperidine, 4,4-difluoropiperidine and pyrrolidine. Especially preferred are morpholine and 4,4-difluoropiperidine.

Further preferred compounds of formula I of the present invention are those, wherein
$R^1$ is selected from the group consisting of
lower alkyl, lower alkenyl, lower alkynyl,
cycloalkyl, lower cycloalkylalkyl,
lower hydroxyalkyl, lower alkoxyalkyl,
lower alkylsulfanylalkyl,
lower dialkylaminoalkyl, lower dialkylcarbamoylalkyl,
phenyl unsubstituted or substituted with one or two groups independently selected from lower alkyl, lower halogenoalkoxy or lower hydroxyalkyl,
lower phenylalkyl wherein the phenyl ring may be unsubstituted or substituted with one or two groups independently selected from lower alkyl, halogen, lower alkoxy or lower hydroxyalkyl, lower heteroarylalkyl wherein the heteroaryl ring may be unsubstituted or substituted with one or two groups independently selected from lower alkyl, halogen, lower alkoxy or lower hydroxyalkyl and
lower heterocyclylalkyl wherein the heterocycly ring may be unsubstituted or substituted with one or two lower alkyl groups and
$R^2$ is hydrogen or lower alkyl.

More preferred are compounds of formula I, wherein
$R^1$ is selected from the group consisting of
lower alkyl,
cycloalkyl, lower cycloalkylalkyl,
lower alkoxyalkyl and
lower phenylalkyl wherein the phenyl ring may be unsubstituted or substituted with one or two groups independently selected from lower alkyl, halogen, lower alkoxy or lower hydroxyalkyl and $R^2$ is hydrogen or lower alkyl.

Especially preferred are those compounds of formula I, wherein $R^1$ is lower phenylalkyl wherein the phenyl ring may be unsubstituted or substituted with one or two groups independently selected from lower alkyl, halogen, lower alkoxy or lower hydroxyalkyl and $R^2$ is hydrogen or lower alkyl.

Also preferred are compounds of formula I, wherein $R^1$ and $R^2$ are lower alkyl.

Furthermore, compounds of formula I according to the present invention are preferred, wherein $R^3$ is selected from the group consisting of
hydrogen, lower alkyl, lower hydroxyalkyl, lower alkoxyalkyl, lower halogenoalkyl, lower
cycloalkylalkyl, lower cyanoalkyl,
lower alkylsulfonyl and
phenyl unsubstituted or substituted with one or two groups independently selected from lower alkyl, halogen, lower alkoxy, lower halogenoalkoxy and lower hydroxyalkyl.

More preferred are those compounds of formula I wherein $R^3$ is selected from the group consisting of hydrogen, lower alkyl, lower halogenoalkyl, lower cycloalkylalkyl and lower cyanoalkyl, with those compounds, wherein $R^3$ is lower halogenoalkyl, being especially preferred. Compounds of formula I, wherein $R^3$ is hydrogen are also preferred.

$R^4$ is hydrogen or halogen. Compounds of formula I, wherein $R^4$ is selected from the group consisting of hydrogen, chloro and bromo, are preferred.

Especially preferred compounds of formula I according to the invention are those, wherein $R^4$ is hydrogen.

Further preferred compounds of formula I according to the present invention are those compounds, wherein G signifies

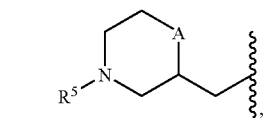

G1 wherein $R^5$ is selected from lower alkyl, cycloalkyl, lower cycloalkylalkyl and lower phenylalkyl and A is selected from $CH_2$, O and S.

Within this group, those compounds of formula I are preferred, wherein A is O. Also preferred are those, wherein A is $CH_2$. $R^5$ is preferably lower alkyl.

Also preferred are compounds of formula I, wherein G is a group selected from G2, G3 and G4.

Especially preferred are compounds of formula I, wherein G signifies

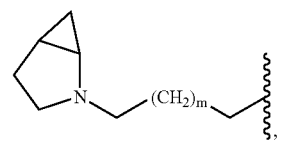

G2 wherein m is 0, 1 or 2. Preferably, m is 1.

Furthermore, compounds of formula I are preferred, wherein G signifies

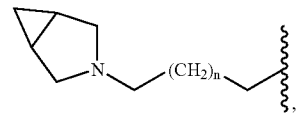

G3 wherein n is 0, 1 or 2. Preferably, n is 1.

Also preferred are compounds of formula I, wherein G signifies

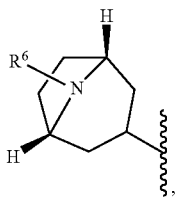

G4 wherein $R^6$ is lower alkyl or cycloalkyl.

Within this group those compounds of formula I are preferred, wherein $R^6$ is lower alkyl. More preferably, $R^6$ signifies isopropyl.

Particularly preferred compounds of formula I are the following:

[5-(4-isopropyl-morpholin-2-ylmethoxy)-1-(2,2,2-trifluoro-ethyl)-1H-indol-2-yl]-morpholin-4-yl-methanone,
[5-((R)-1-isopropyl-piperidin-3-ylmethoxy)-1-(2,2,2-trifluoro-ethyl)-1H-indol-2-yl]-morpholin-4-yl-methanone,
[5-((S)-1-isopropyl-piperidin-3-ylmethoxy)-1-(2,2,2-trifluoro-ethyl)-1H-indol-2-yl]-morpholin-4-yl-methanone,
{5-[3-(2-aza-bicyclo[3.1.0]hex-2-yl)-propoxy]-1H-indol-2-yl}-morpholin-4-yl-methanone,
{5-[3-(3-aza-bicyclo[3.1.0]hex-3-yl)-propoxy]-1H-indol-2-yl}-morpholin-4-yl-methanone,
[5-[3-(3-aza-bicyclo[3.1.0]hex-3-yl)-propoxy]-1-(2,2,2-trifluoro-ethyl)-1H-indol-2-yl]-morpholin-4-yl-methanone,
3-endo-[5-(8-isopropyl-8-aza-bicyclo[3.2.1]oct-3-yloxy)-1-(2,2,2-trifluoro-ethyl)-1H-indol-2-yl]-morpholin-4-yl-methanone,
3-endo-(4,4-difluoro-piperidin-1-yl)-[5-(8-isopropyl-8-aza-bicyclo[3.2.1]oct-3-yloxy)-1-(2,2,2-trifluoro-ethyl)-1H-indol-2-yl]-methanone, and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbent or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises reacting a compound of the formula II

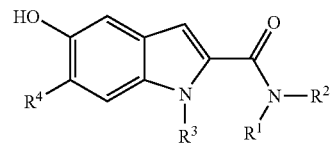

II wherein $R^1$ to $R^4$ are as defined herein before, with an alcohol of the formula III

HO-G  III wherein G is as defined herein before, in the presence of a trialkylphosphine or triphenylphosphine and of an azo compound to obtain a compound of the formula I

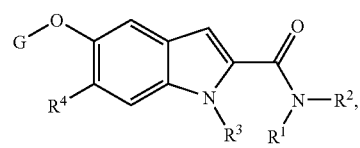

I wherein $R^1$ to $R^4$ and G are as defined herein before, and if desired, converting the compound obtained into a pharmaceutically acceptable acid addition salt.

In more detail, the compounds of formula I can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The preparation of compounds of formula I of the present invention may be carried out in sequential or convergent synthetic routes. Syntheses of the invention are shown in the following schemes. The skills required for carrying out the reaction and purification of the resulting products are known to those in the art. The substituents and indices used in the following description of the processes have the significance given above unless indicated to the contrary.

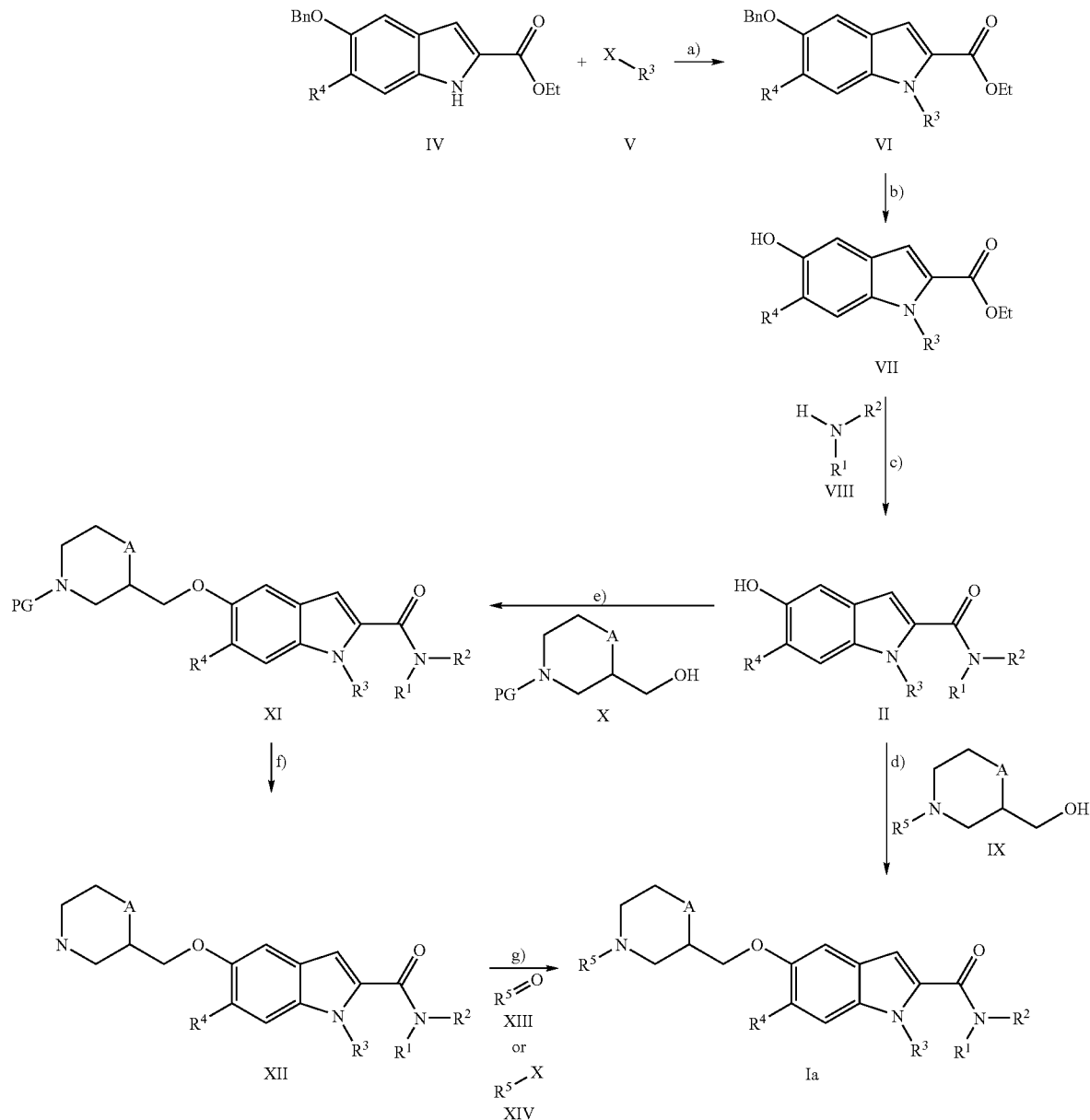

Scheme 1

Compounds of general formula I can be prepared according to scheme 1 as follows:

Compounds IV can be optionally subjected to reactions in which the indole NH will be substituted by lower alkyl substituents benzyl substituents, alkyl and arylsulfonyl substituent through a reaction with an alkylating agent V. Conditions commonly used in such types of transformation are widely described in literature and known to those in the art. The group X can be any halogen (chlorine, bromine or iodine) or pseudo halogen (e.g. trifluoromethylmethanesulfonyl, para-toluenesulfonyl, methanesulfonyl and the like). The reaction might be carried out in the presence or absence of a solvent and preferably in the presence of a base. Solvents like N,N-dimethyl acetamide, N,N-dimethylformamide, tetrahydrofuran, diethyl ether, dioxane, acetonitrile, butanone and the like are conveniently used. There is no particular restriction on the nature of the solvent to be employed, provided that it has no adverse effect on the reaction or the reagents involved and that it can dissolve the reagents, at least to some extent. Usually the reaction is carried out in the presence of a base. Suitable bases include sodium hydride, diisopropylethylamine, sodium carbonate, cesium carbonate and the like. The reaction can take place over a wide range of temperatures and the precise reaction temperature is not critical to the invention. It is preferred to carry out the reaction with heating from ambient temperature to reflux. The time required for the reaction may also vary widely, depending on many factors, notably the reaction temperature and the nature of the reagents. However, a period of from 0.5 h to several days will usually suffice to yield the title compounds VI.

Alternatively, compound IV can be alkylated or arylated by a boronic acid or a boronic ester of formula V (either commercially available or accessible by methods described in references or by methods known in the art, as appropriate). Conditions commonly used in such types of transformation are described in literature and known to those in the art (e.g. Mederski, W. W. K. R.; Lefort, M.; Germann, M. Kux, D. Tetrahedron 1999 55 12757). R1 can be any aryl, cycloalkyl or heteroaryl compounds. The group X can be a boronic acid $B(OH)_2$ or a boronate $B(OR)_2$ and $R^3$ can be any aryl, cycloalkyl or heteroaryl compounds.

Alternatively, compound IV can be arylated by compound V (either commercially available or accessible by methods described in references or by methods known in the art; as appropriate). The transformation can be affected by employing reaction conditions which are known to those in the art and widely described (e.g. Watanabe, M; Nishiyama, M.; Yamamoto, T.; Koie, Y, Tetrahedron Letters 2000, 41, 481; Old, D. W.; Harris, M. C.; Buchwald, S. L 2000 2 10 1403; Klapars, A.; Antilla, J. C.; Huang, X.; Buchwald, S. L. J. Am. Chem. Soc. 2001 123 7727). The group X can be any halogen group (chlorine, bromine, iodine) or pseudo halogen group (e.g. trifluoromethylmethanesulfonyl, paratoluensulfonyl, methanesulfonyl and the like) and $R^3$ can be any aryl or heteroaryl compounds.

Removal of the benzyl protective groups is performed using conditions commonly used in such types of transformation and is widely described in literature and known to those in the art (For reaction conditions described in literature affecting such reactions see for example: Protective groups in organic synthesis, 3rd Edition, Theodora W. Greene, Peter G. M. Wuts, Wiley Interscience 1999). It is preferred to use palladium adsorbed on activated charcoal as catalyst in suitable solvent e.g. ethyl acetate, tetrahydrofuran, methanol and the like, alone or in mixture. Hydrogen gas is present under a partial pressure from 1 atm to 100 atm, yielding a compound of formula VII.

The compounds of formula VII are transformed into the free acids under basic conditions, for example by using lithium hydroxide monohydrate as a base.

The coupling of carboxylic acids with amines is widely described in literature and the procedures are known to those in the art (For reaction conditions described in literature affecting such reactions see for example: Comprehensive Organic Transformations: A Guide to Functional Group Preparations, 2nd Edition, Richard C. Larock, John Wiley & Sons, New York, N.Y. 1999). Carboxylic acid can conveniently be transformed to the respective amide through coupling with an amine VIII (either commercially available or accessible by methods described in references or by methods known in the art, as appropriate) by employing the usage of coupling reagents. For example coupling reagents like N,N'-carbonyldiimidazole, N,N'-dicyclohexylcarbodiimide, 1-(3-dimethylaminopropyl)-3-ethylcarbodiimide hydrochloride, 1-[bis(dimethylamino)methylene]-1H-1,2,3-triazolo[4,5-b]pyridinium-3-oxide hexafluorophosphate, 1-hydroxy-1,2,3-benzotriazole, O-benzotriazol-1-yl-N,N,N',N'-tetramethyluronium tetrafluoroborate and the like can equally be employed to affect such transformation. It is preferred to carry out the reaction in a solvent like dimethylformamide and in the presence of a base. There is no particular restriction on the nature of the solvent to be employed, provided that it has no adverse effect on the reaction or the reagents involved and that it can dissolve the reagents, at least to some extent. Examples of suitable solvents include: dimethylformamide, dichloromethane, dioxane, tetrahydrofuran and the like. There is no particular restriction on the nature of the base used in this stage and any base commonly used in this type of reaction may equally be employed here. Examples of such bases include triethylamine and diisopropylethylamine and the like. The reaction can take place over a wide range of temperatures and the precise reaction temperature is not critical to the invention. It is preferred to carry out the reaction with heating from ambient temperature to reflux. The time required for the reaction may also vary widely, depending on many factors, notably the reaction temperature and the nature of the reagents. However, a period of time from 0.5 h to several days will usually suffice to yield amide derivatives II.

The syntheses of ethers are widely described in literature and the procedures are known to those in the art (For reaction conditions described in literature affecting such reactions see for example: Comprehensive Organic Transformations: A Guide to Functional Group Preparations, 2nd Edition, Richard C. Larock, John Wiley & Sons, New York, N.Y. 1999). The transformation can be affected by employing reaction conditions which are commonly utilised in the so-called "Mitsunobu reaction" which is known to those in the art and widely described (Hughes, David L. The Mitsunobu reaction. Organic Reactions, New York, 1992 42 335-656.) It is preferred to couple amide II with alcohols IX bearing a lower alkyl group $R^5$ (either commercially available or accessible by methods described in references or by methods known in the art, as appropriate) under conditions employing a phosphine like a trialkylphosphine such as tributylphosphine, triphenylphosphine and the like and a diazo-compound like diethyl-azodicarboxylate, diisopropyl-azodicarboxylate (optionally polymer bound), di-tert-butylazodicarboxylate, tetramethyl azodicarboxamide and the like in a solvent commonly used in such transformations like tetrahydrofuran, toluene, dichloromethane and the like. There is no particular restriction on the nature of the solvent to be employed, provided that it has no adverse effect on the reaction or the reagents involved and that it can dissolve the reagents, at least to some extent. The reaction can take place over a wide range of temperatures and the precise reaction temperature is not critical to the invention. It is preferred to carry out the reaction with heating from ambient temperature to reflux. The time required for the reaction may also vary widely, depending on many factors, notably the reaction temperature and the nature of the reagents. However, a period of from 0.5 h to several days will usually suffice to yield the title compounds Ia.

The ether of formula XI are prepared under the conditions as described under point d) with alcohols X bearing a protective group (either commercially available or accessible by methods described in references or by methods known in the art, as appropriate).

Removal of the protective groups from compound of formula XI, yielding a compound of formula XII, as a free amine or any of its suitable salt (e.g. hydrochloric acid, trifluoroacetic acid) is performed using conditions commonly used in such types of transformation and is widely described in the literature and known to those in the art (For reaction conditions described in the literature affecting such reactions see for example: Theodora W. Greene, Peter G. M. Wuts, Protective groups in organic synthesis, 3rd Edition, Wiley Interscience 1999).

Introduction of a lower alkyl substituent yielding a compound of formula Ia can be carried out using reductive amination of various ketones or aldehydes XIII with the amine XII as free amine or any of its suitable salt (e.g. hydrochloric acid, trifluoroacetic acid). The reductive amination is widely described in literature and the procedures are known to those in the art (For reaction conditions described in literature affecting such reactions see for example: Trost, B. M.; Fleming, I., Comprehensive Organic Synthesis, Ed. Pergamon Press 1991 or Zaragoza, F., Stephensen, H., Knudsen, S. M., Pridal, L., Wulff, B. S., Rimvall, K. Journal of Medicinal Chemistry 2004, 47, 2833 or A. F. Abdel-Magid, K. G. Carson, B. D. Harris, C. A. Maryanoff and R. K. Shah, Journal of Organic Chemistry, 1996, 61, 3849).

Alternatively, the amine XII as free amine or any of its suitable salt (e.g. hydrochloric acid, trifluoroacetic acid) is conveniently alkylated with a suitable alkylating reagent XIV under basic conditions to give access to the indole derivatives Ia.

A synthesis of compounds of formula I, wherein G signifies G2, is shown in scheme 2.

The ethers of formula XVIII are prepared from 5-hydroxy-indole-2-carboxylic acid ethyl ester XV and a suitable halogeno- or pseudohalogenoalcohol XVI under the conditions described under point d).

Alternatively, they can be prepared by alkylation of 5-hydroxy-indole-2-carboxylic acid ethyl ester XV using bis-halogeno (chlorine, bromine, iodine) or pseudohalogenoalkanes XVII (e.g. trifluoromethylmethanesulfonyl, paratoluensulfonyl, methanesulfonyl and the like) under the conditions described under point a).

The amides of formula XIX are prepared under the conditions described under point c).

Compounds of formula Ib are prepared from a compound of formula XIX and 2-aza-bicyclo[3.1.0]hexane hydrochloride XX under the conditions described under point a). The preparation of 2-aza-bicyclo[3.1.0]hexane and its salt XX (CAS Registry Nos. 841302-37-2 and 27202-71-7) is known in the literature (e.g. Hamann, Lawrence G.; Khanna, Ashish; Kirby, Mark S.; Magnin, David R.; Simpkins, Ligaya M.; Sutton, James C.; Robl, Jeffrey, Preparation of adamantyglycinamide inhibitors of dipeptidyl peptidase IV, WO 2005012249A2, 2005).

The indoles Ib might be the desired products, however, they might optionally be subjected to a subsequent alkylating reaction as described above under point a) to furnish the desired compounds Ic.

Compounds of formula I, wherein G signifies G3, can be prepared according to the method described in scheme 3.

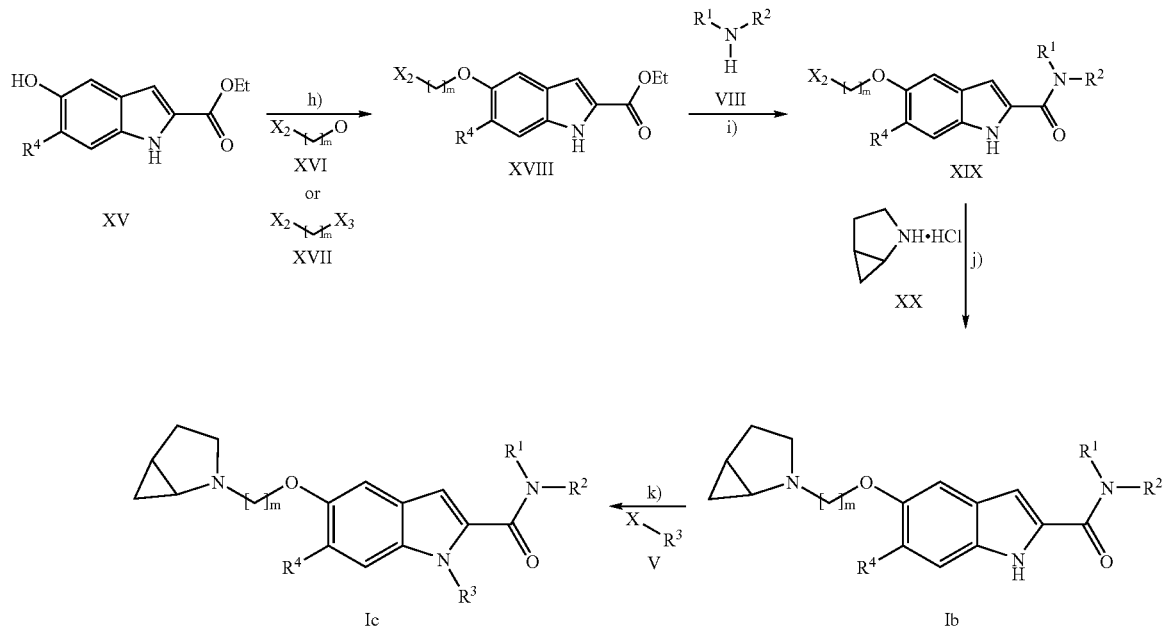

Scheme 2

Scheme 3

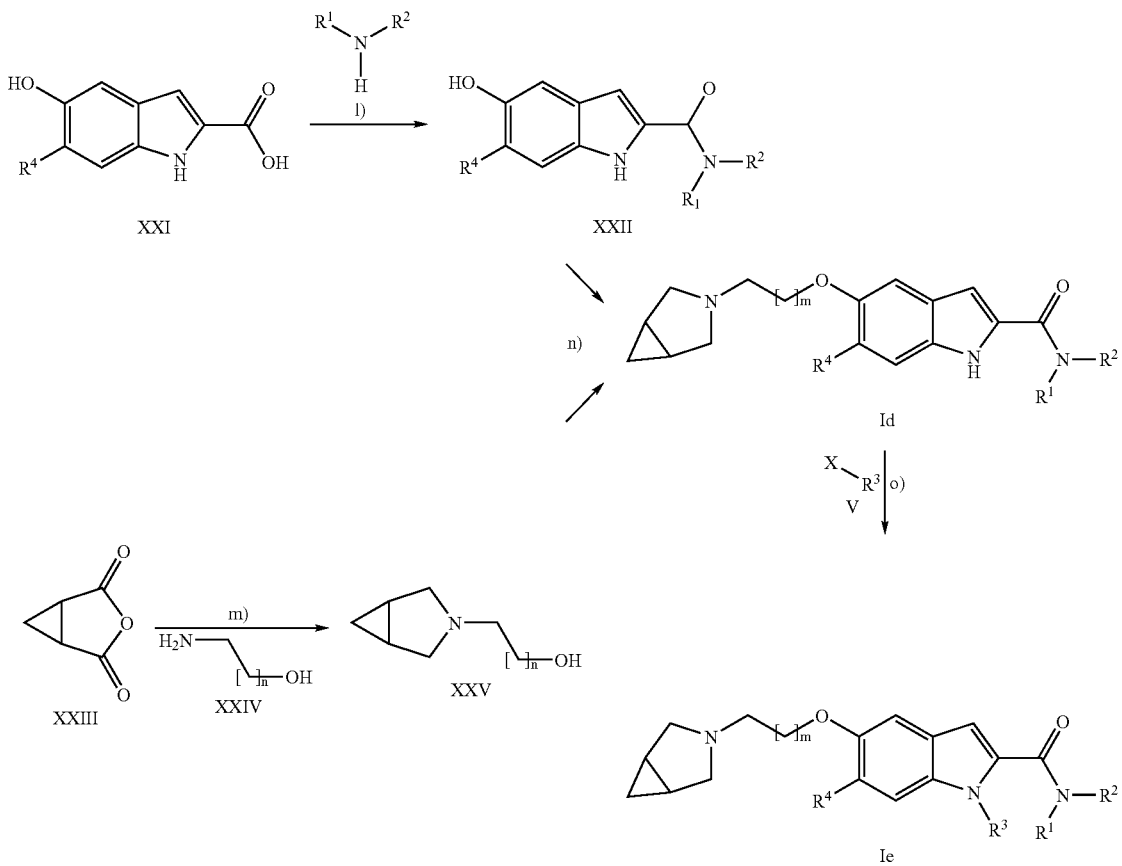

The coupling of carboxylic acids with amines is widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). Carboxylic acid XXI can conveniently be transformed to the respective amide through coupling with an amine VIII (either commercially available or accessible by methods described in references or by methods known in the art, as appropriate) by employing the usage of coupling reagents. For example coupling reagents like N,N'-carbonyldiimidazole, N,N'-dicyclohexyl-carbodiimide, 1-(3-dimethylaminopropyl)-3-ethylcarbodiimide hydrochloride, 1-[bis(dimethylamino)methylene]-1H-1,2,3-triazolo[4,5-b]pyridinium-3-oxide hexafluorophosphate, 1-hydroxy-1,2,3-benzotriazole, O-benzotriazol-1-yl-N,N,N',N'-tetramethyluronium tetrafluoroborate and the like can equally be employed to affect such transformation. It is preferred to carry out the reaction in a solvent like dimethylformamide and in the presence of a base. There is no particular restriction on the nature of the solvent to be employed, provided that it has no adverse effect on the reaction or the reagents involved and that it can dissolve the reagents, at least to some extent. Examples for suitable solvents include: dimethylformamide, dichloromethane, dioxane, tetrahydrofuran and the like. There is no particular restriction on the nature of the base used in this stage and any base commonly used in this type of reaction may equally be employed here. Examples of such bases include triethylamine and diisopropylethylamine and the like. The reaction can take place over a wide range of temperatures and the precise reaction temperature is not critical to the invention. It is preferred to carry out the reaction with heating from ambient temperature to reflux. The time required for the reaction may also vary widely, depending on many factors, notably the reaction temperature and the nature of the reagents. However, a period of from 0.5 h to several days will usually suffice to yield amide derivatives XXII.

The compounds of formula XXV may be prepared from commercially available cyclopropane-2,3-dicarboxylic acid anhydride XXIII and a suitable aminoalcohol XXIV by amide introduction followed by a reduction. These methods are described in literature and known to those in the art (For reaction conditions described in the literature e.g. Kollmeyer, Willy D., 3-Benzyl-3-azabicyclo(3.1.0)hexane-2,4-dione, U.S. Pat. No. 4,183,857, 1980)

The ether derivatives of formula Id are prepared under the conditions described under point d).

The indoles Id might be the desired products, however, they might optionally be subjected to a subsequent alkylating reaction as described above under point a) to furnish the desired compounds Ie.

Compounds of formula I, wherein G signifies G4, may be prepared according to the methods described in scheme 4.

Scheme 4

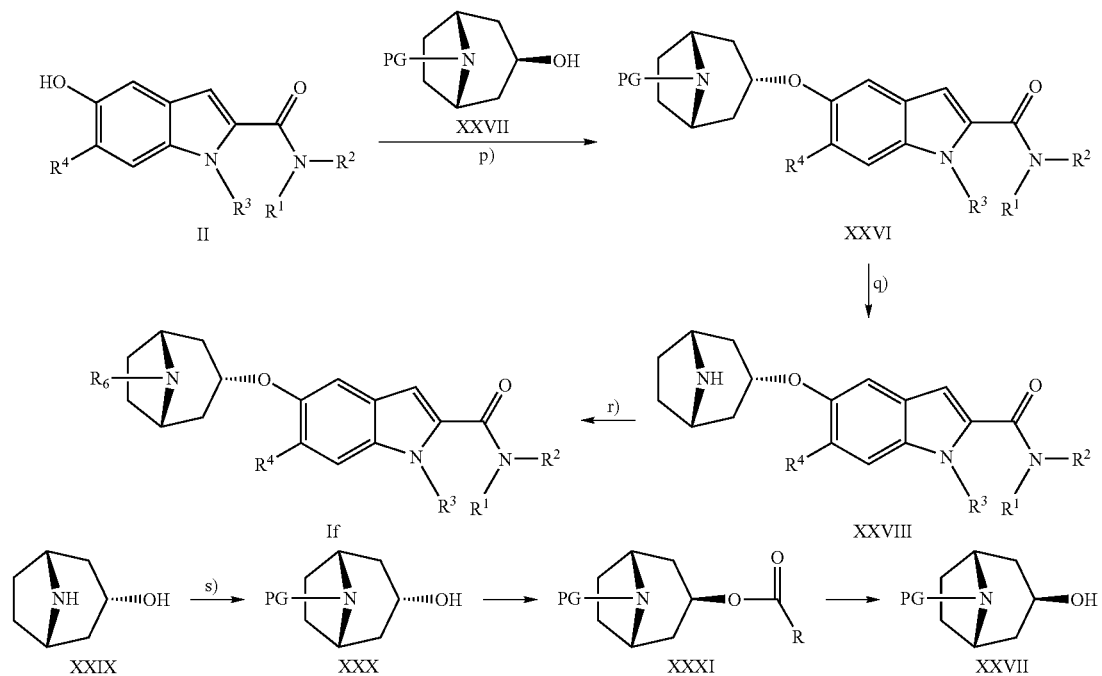

The compounds of formula XXVI may be prepared by coupling a compound of formula II with a suitably protected alcohol of formula XXVII as described under point d).

The compounds of formula XXVIII maybe obtained from compounds of formula XXVI by removal of the protecting group PG under suitable deprotection conditions, as described under point f), for example using a solution of hydrochloric acid in ethyl acetate when the protecting group is tert-butyloxycarbonyl (other acids such as trifluoroacetic acid, phosphoric acid, p-toluenesulfonic acids and the like may also be used); other protecting groups known in the art may be removed by appropriate methods (For reaction conditions described in literature affecting such reactions see for example: Protective groups in organic synthesis, 3rd Edition, Theodora W. Greene, Peter G. M. Wuts, Wiley Interscience 1999). Compounds of formula XXVIII may be isolated as neutral compounds or as salts of organic or inorganic acids.

The compounds of formula XXVIII may be converted into compounds of formula If using methods described under point g).

A suitably protected alcohol of formula XXVII may be prepared from the commercially available nortropine XXIX by introducing a suitable protecting group, for example by reaction with tert-butyldicarbonate in a suitable solvent, such as tetrahydrofuran, between 0° C. and 80° C., preferably at room temperature, or according to other methods known in the art, to afford compounds of formula XXX. Other protecting groups are suitable (For reaction conditions described in the literature affecting such protecting groups, see for example: Theodora W. Greene, Peter G. M. Wuts, Protective groups in organic synthesis, 3rd Edition, Wiley Interscience 1999). Compounds of formula XXX are converted to esters of formula XXXI by reaction with a suitable carboxylic acid (such as 4-nitrobenzoic acid) in the presence of a phosphine and diazo-compound. The transformation may be effected by employing reaction conditions which are commonly utilised in the so-called "Mitsunobu reaction" which is known to those in the art and widely described (Hughes, David L. The Mitsunobu reaction. Organic Reactions, New York, 1992 42 335-656.), as outlined in point d). Compounds of formula XXVII are obtained from compounds of formula XXXI by hydrolysis of the ester under conditions known in the art, for example using lithium hydroxide monohydrate in a suitable solvent or solvent mixture such as for example methanol or water and tetrahydrofuran, or using other methods known in the art.

As described above, the compounds of formula I of the present invention can be used as medicaments for the treatment and/or prevention of diseases which are associated with the modulation of H3 receptors.

In this context, the expression 'diseases associated with the modulation of H3 receptors' means diseases which can be treated and/or prevented by modulation of H3 receptors. Such diseases encompass, but are not limited to, obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy and other diseases including asthma, allergy, allergy-induced airway responses, congestion, chronic obstructive pulmonary disease and gastro-intestinal disorders.

In a preferable aspect, the expression 'diseases associated with modulation of H3 receptors' relates to obesity, metabolic syndrome (syndrome X) and other eating disorders, with obesity being especially preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors.

In another embodiment, the invention relates to a method for the treatment and/or prevention of diseases which are associated with the modulation of H3 receptors, which method comprises administering a therapeutically active amount of a compound of formula I to a human being or animal. A method for the treatment and/or prevention of obesity is preferred.

The invention further relates to the use of compounds of formula I as defined above for the treatment and/or prevention of diseases which are associated with the modulation of H3 receptors.

In addition, the invention relates to the use of compounds of formula I as defined above for the preparation of medicaments for the treatment and/or prevention of diseases which are associated with the modulation of H3 receptors. The use of compounds of formula I as defined above for the preparation of medicaments for the treatment and/or prevention of obesity is preferred.

Furthermore, the present invention relates to the use of a compound of formula I for the manufacture of a medicament for the treatment and prevention of obesity in a patient who is also receiving treatment with a lipase inhibitor and particularly, wherein the lipase inhibitor is orlistat.

It is a further preferred embodiment of the present invention to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include, but are not limited to, anorectic agents, lipase inhibitors, selective serotonin reuptake inhibitors (SSRI) and agents that stimulate metabolism of body fat. Combinations or associations of the above agents may be encompassing separate, sequential or simultaneous administration.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to tetrahydrolipstatin. Administration of a therapeutically effective amount of a compound according to formula I in combination or association with a therapeutically effective amount of tetrahydrolipstatin is especially preferred.

Tetrahydrolipstatin (orlistat) is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 0 185 359, 0 189 577, 0 443 449 and 0 524 495.

Suitable anorectic agents of use in combination with a compound of the present invention include, but are not limited to, APD356, aminorex, amphechloral, amphetamine, axokine, benzphetamine, bupropion, chlorphentermine, clobenzorex, cloforex, clominorex, clortermine, CP945598, cyclexedrine, CYT009-GhrQb, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, metreleptin, norpseudoephedrine, pentorex, phendimetrazine, phenmetrazine, phentermine, phenylpropanolamine, picilorex, rimonabant, sibutramine, SLV319, SNAP 7941, SR147778 (Surinabant), steroidal plant extract (e.g. P57) and TM30338 and pharmaceutically acceptable salts thereof.

Most preferable anorectic agents are sibutramine, rimonabant and phentermine.

Suitable selective serotonin reuptake inhibitors of use in combination with a compound of the present invention include: fluoxetine, fluvoxamine, paroxetine and sertraline and pharmaceutically acceptable salts thereof.

Suitable agents that stimulate metabolism of body fat include, but are not limited to, growth hormone agonist (e.g. AOD-9604).

The use of a compound of formula I in the manufacture of a medicament for the treatment and prevention of obesity in a patient who is also receiving treatment with a compound selected from the group consisting of a lipase inhibitor, an anorectic agent, a selective serotonin reuptake inhibitor and an agent that stimulates metabolism of body fat, is also an embodiment of the present invention.

The use of a compound of formula I in the manufacture of a medicament for the treatment and prevention of obesity in a patient who is also receiving treatment with a lipase inhibitor, preferably with tetrahydrolipstatin, is also an embodiment of the present invention.

It is a further preferred embodiment to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of a lipase inhibitor, particularly, wherein the lipase inhibitor is tetrahydrolipstatin. Also an embodiment of the invention is the method as described above for the simultaneous, separate or sequential administration of a compound according to formula I and a lipase inhibitor, particularly tetrahydrolipstatin.

It is a further preferred embodiment to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of an anti-diabetic agent.

The term "anti-diabetic agent" refers to compounds selected from the group consisting of 1) PPARγ agonists such as pioglitazone (actos) or rosiglitazone (avandia) and the like; 2) biguanides such as metformin (glucophage) and the like; 3) sulfonylureas such as glibenclamide, glimepiride (amaryl), glipizide (glucotrol), glyburide (DiaBeta) and the like; 4) nonsulfonylureas such as nateglinide (starlix), repaglimide (prandin) and the like; 5) PPARα/γ agonists such as GW-2331 and the like 6) DPP-IV-inhibitors such as LAF-237 (vildagliptin), MK-0431, BMS-477118 (saxagliptin) or GSK23A and the like; 7) Glucokinase activators such as the compounds disclosed in e.g. WO 00/58293 A1 and the like; 8) α-Glucosidase inhibitors such as acarbose (precose) or miglitol (glyset) and the like.

Also an embodiment of the invention is the method as described above for the simultaneous, separate or sequential administration of a compound according to formula I and a therapeutically effective amount of an anti-diabetic agent.

The use of a compound of formula I in the manufacture of a medicament for the treatment and prevention of Type II diabetes in a patient who is also receiving treatment with an anti-diabetic agent is also an embodiment of the present invention.

It is a further preferred embodiment to provide a method of treatment or prevention of dyslipidemias in a human which comprises administration of a therapeutically effective amount of a compound according to formula I in combination or association with a therapeutically effective amount of a lipid lowering agent.

The term "lipid lowering agent" refers to compounds selected from the group consisting of 1) bile acid sequestrants such as cholestyramine (questran), colestipol (colestid) and the like; 2) HMG-CoA reductase inhibitors such as atorvastatin (lipitor), cerivastatin (baycol), fluvastatin (lescol), pravastatin (pravachol), simvastatin (zocor) and the like; 3) cholesterol absorption inhibitors such as ezetimibe and the like; 4) CETP inhibitors such as torcetrapib, JTT 705 and the like; 5) PPARα-agonists such as beclofibrate, gemfibrozil (lopid), fenofibrate (lipidil), bezafibrate (bezalip) and the like; 6) lipoprotein synthesis inhibitors such as niacin and the like; and 7) niacin receptor agonists such as nicotinic acid and the like.

Also an embodiment of the invention is the method as described above for the simultaneous, separate or sequential administration of a compound according to formula I and a therapeutically effective amount of a lipid lowering agent.

The use of a compound of formula I in the manufacture of a medicament for the treatment and prevention of dyslipidemia in a patient who is also receiving treatment with a lipid lowering agent, is also an embodiment of the present invention.

It is a further preferred embodiment to provide a method of treatment or prevention of hypertension in a human which comprises administration of a therapeutically effective amount of a compound according to formula I in combination or association with a therapeutically effective amount of an anti-hypertensive agent.

The term "anti-hypertensive agent" or "blood-pressure lowering agent" refers to compounds selected from the group consisting of 1) Angiotensin-converting Enzyme (ACE) Inhibitors including benazepril (lotensin), captopril (capoten), enalapril (vasotec), fosinopril (monopril), lisinopril (prinivil, zestril), moexipril (univasc), perindopril (coversum), quinapril (accupril), ramipril (altace), trandolapril (mavik) and the like; 2) Angiotensin II Receptor Antagonists including candesartan (atacand), eprosartan (teveten), irbesartan (avapro), losartan (cozaar), telmisartan (micadisc), valsartan (diovan) and the like; 3) Adrenergic Blockers (peripheral or central) such as the beta-adrenergic blockers including acebutolol (sectrol), atenolol (tenormin), betaxolol (kerlone), bisoprolol (zebeta), carteolol (cartrol), metoprolol (lopressor; toprol-XL), nadolol (corgard), penbutolol (levatol), pindolol (visken), propranolol (inderal), timolol (blockadren) and the like; alpha/beta adrenergic blockers including carvedilol (coreg), labetalol (normodyne) and the like; alpha-1 adrenergic blockers including prazosin (minipress), doxazosin (cardura), terazosin (hytrin), phenoxybenzamine (dibenzyline) and the like; peripheral adrenergic-neuronal blockers including guanadrel (hylorel), guanethidine (ismelin), reserpine (serpasil) and the like; alpha-2 adrenergic blockers including a-methyldopa (aldomet), clonidine (catapres), guanabenz (wytensin), guanfacine (tenex) and the like; 4) Blood Vessel Dilators (Vasodilators) including hydralazine (apresoline), minoxidil (lonitren), clonidine (catapres) and the like; 5) Calcium Channel Blockers including amlodipine (norvasc), felodipine (plendil), isradipine (dynacirc), nicardipine (cardine sr), nifedipine (procardia, adalat), nisoldipine (sular), diltiazem (cardizem), verapamil (isoptil) and the like; 6) Diuretics such as thiazides and thiazides-like agents, including hydrochlorothiazide (hydrodiuril, microzide), chlorothiazide (diuril), chlorthalidone (hygroton), indapamide (lozol), metolazone (mykrox) and the like; loop diuretics, such as bumetanide (bumex) and furosemide (lasix), ethacrynic acid (edecrin), torsemide (demadex) and the like; potassium-sparing diuretics including amiloride (midamor), triamterene (dyrenium), spironolactone (aldactone) and the tiamenidine (symcor) and the like; 7) Tyrosine Hydroxylase Inhibitors, including metyrosine (demser) and the like; 8) Neutral Endopeptidase Inhibitors, including BMS-186716 (omapatrilat), UK-79300 (candoxatril), ecadotril (sinorphan), BP-1137 (fasidotril), UK-79300 (sampatrilat) and the like; and 9) Endothelin Antagonists including tezosentan (RO0610612), A308165 and the like.

Also an embodiment of the invention is the method as described above for the simultaneous, separate or sequential administration of a compound according to formula I and a therapeutically effective amount of a anti-hypertensive agent.

The use of a compound of formula I in the manufacture of a medicament for the treatment and prevention of hypertension in a patient who is also receiving treatment with an anti-hypertensive agent, is also an embodiment of the present invention.

As described above, the compounds of formula I and their pharmaceutically acceptable salts possess valuable pharmacological properties. Specifically, it has been found that the compounds of the present invention are good histamine 3 receptor (H3R) antagonists and/or inverse agonists.

The following test was carried out in order to determine the activity of the compounds of formula (I).

Binding assay with $^3$H-(R)α-methylhistamine

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 μg protein/well) was incubated with increasing concentrations of $^3$H(R) α-Methylhistamine di-hydrochloride (0.10 to 10 nM). Non-specific binding was determined using a 200 fold excess of cold (R)α-methylhistamine dihydrobromide (500 nM final concentration). The incubation was carried out at room temperature (in deep-well plates shaking for three hours). The final volume in each well was 250 μl. The incubation was followed by rapid filtration on GF/B filters (pre-soaked with 100 μl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then scintillation fluid (Microscint 40, 40 microl in each well) was added and the amount of radioactivity on the filter was determined with a Packard top-counter after shaking the plates for two hours at 200 rpm at room temperature.

Binding Buffer: 50 mM Tris-HCl pH 7.4 and 5 mM $MgCl_2 \times 6H_2O$ pH 7.4. Washing Buffer: 50 mM Tris-HCl pH 7.4 and 5 mM $MgCl_2 \times 6H_2O$ and 0.5 M NaCl pH 7.4.

Indirect measurement of affinity of H3R inverse agonists: twelve increasing concentrations (ranging from 10 µM to 0.3 nM) of the selected compounds were always tested in competition binding experiments using membrane of the human HR3-CHO cell line. An appropriate amount of protein, e.g. approximately 500 cpm binding of RAMH at Kd, were incubated for 1 hour at room temperature in 250 µl final volume in 96-well plates in presence of $^3H(R)\alpha$-methylhistamine (1 nM final concentration=Kd). Non-specific binding was determined using a 200 fold excess of cold (R)α-methylhistamine dihydrobromide.

All compounds were tested at a single concentration in duplicates. Compounds that showed an inhibition of [$^3$H]-RAMH of more than 50% were tested again to determine $IC_{50}$ in a serial dilution experiment. Ki's were calculated from $IC_{50}$ based on Cheng-Prusoff equation (Cheng, Y, Prusoff, W H (1973) Biochem Pharmacol 22, 3099-3108).

The compounds of the present invention exhibit $K_i$ values within the range of about 0.1 nM to about 1000 nM, preferably of about 0.1 nM to about 100 nM and more preferably of about 0.1 nM to about 30 nM. The following table shows measured values for some selected compounds of the present invention.

|  | $K_i$ (nM) |
| --- | --- |
| Example 1 | 30 |
| Example 5 | 40 |
| Example 6 | 26 |

Demonstration of additional biological activities of the compounds of the present invention may be accomplished through in vitro, ex vivo and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoA1 mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein and serum triglyceride levels are determined.

Method for Measuring HDL-Cholesterol Levels

To determine plasma HDL-cholesterol levels, hApoA1 mice are bled and grouped with equivalent mean plasma HDL-cholesterol levels. The mice are orally dosed once daily with vehicle or test compound for 7 to 14 days and then bled on the following day. Plasma is analyzed for HDL-cholesterol.

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable salts and esters, into a galenical administration form together with suitable, non-toxic, inert, therapeutically compatible solid or liquid carrier materials and if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants-come into consideration as pharmaceutical adjuvants.

The dosage of the compounds of formula (I) can vary within wide limits depending on the disease to be controlled, the age and the individual condition of the patient and the mode of administration and will, of course, be fitted to the individual requirements in each particular case. For adult patients a daily dosage of about 1 mg to about 1000 mg, especially about 1 mg to about 100 mg, comes into consideration. Depending on the dosage it is preferable to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Intermediates

Intermediate 1

[5-Hydroxy-1-(2,2,2-trifluoro-ethyl)-1H-indol-2-yl]-morpholin-4-yl-methanone

Step 1: 5-Benzyloxy-1-(2,2,2-trifluoro-ethyl)-1H-indole-2-carboxylic acid ethyl ester A solution of 5-benzyloxyindole-2-carboxylic acid ethyl ester (purchased at Biosynth, ref B2000, 2.26 g, 1.0 eq.) in dimethylformamide (15 mL) was added to a suspension of sodium hydride (60% dispersion in oil, 367 mg, 1.2 eq.) in dimethylformamide. The reaction mixture was stirred 50 min at 70° C. 2,2,2-Trifluoroethyltrifluoromethanesulfonate (3.0 g, 1.7 eq.) was added and the reaction mixture was stirred overnight at 70° C. The reaction mixture was partitioned between ethyl acetate and water. The aqueous layer was extracted with ethyl acetate and the combined organic fractions were washed with water and brine, evaporated to dryness and purified on silica eluting with 9:1 cyclohexane/ethyl acetate to yield 1.9 g (66%) of the desired product as light yellow solid. MS (m/e): 378.5 (MH$^+$, 100%).

Step 2: 5-Hydroxy-1-(2,2,2-trifluoro-ethyl)-1H-indole-2-carboxylic acid ethyl ester A mixture of 5-benzyloxy-1-(2,2,2-trifluoro-ethyl)-1H-indole-2-carboxylic acid ethyl ester (intermediate 1, step a, 13.6 g, 1.0 eq.) and palladium on activated charcoal (10% by weight, 1.15 g, 0.03 eq.) in ethyl acetate (700 mL), was vigorously stirred for 4 days at room temperature under an atmosphere of hydrogen (1 Atm). The solid was filtered off and washed with ethyl acetate. The filtrate was evaporated to dryness and purified on silica eluting with 1:4 cyclohexane/ethyl acetate to yield 8.6 g (83%) of the desired product as white solid. MS (m/e): 288.5 (MH$^+$, 100%).

Step 3: 5-Hydroxy-1-(2,2,2-trifluoro-ethyl)-1H-indole-2-carboxylic acid

A mixture of 5-hydroxy-1-(2,2,2-trifluoro-ethyl)-1H-indole-2-carboxylic acid ethyl ester (Intermediate 1, step b, 8.5 g, 1.0 eq.), lithium hydroxide monohydrate (1.43 g, 1.15 eq.), water (45 mL), methanol (30 mL) and tetrahydrofuran (90 mL) was heated to reflux for 24 h. The volatiles were removed in vacuo and the resulting solution was acidified (pH ca. 2) with hydrochloric acid (1N). The precipitate was filtered and dried in vacuo to yield 7.65 g (99%) of the desired product as off-white solid. MS (m/e): 258.5 (M–H$^-$, 100%).

Step 4: [5-Hydroxy-1-(2,2,2-trifluoro-ethyl)-1H-indol-2-yl]-morpholin-4-yl-methanone A mixture of 5-hydroxy-1-(2,2,2-trifluoro-ethyl)-1H-indole-2-carboxylic acid (intermediate 1, step c, 7.62 g, 1.0 eq.), 2-(1H-benzotriazole-1-yl)-1,1,3,3-tetramethyluronium tetrafluoroborate (12.8 g, 1.3 eq.), morpholine (3.36 mL, 1.3 eq.) and N-ethyldiisopropylamine (25.7 mL, 5 eq.) in dimethylformamide (85 mL) was stirred at room temperature for 24 h. The reaction mixture was diluted with ethyl acetate and washed with hydrochloric acid (1N), water and brine and dried over sodium sulfate, filtered and concentrated in vacuo. The precipitate was filtered, washed with ethyl acetate and dried in vacuo to yield 7.15 g (74%) of the desired product as off-white solid. MS (m/e): 329.5 (MH$^+$, 100%).

Example 1

[5-(4-Isopropyl-morpholin-2-ylmethoxy)-1-(2,2,2-trifluoro-ethyl)-1H-indol-2-yl]-morpholin-4-yl-methanone Step 1: 2-[2-(Morpholine-4-carbonyl)-1-(2,2,2-trifluoro-ethyl)-1H-indol-5-yloxymethyl]-morpholine-4-carboxylic acid tert-butyl ester To a cold (0° C.) mixture of [5-hydroxy-1-(2,2,2-trifluoro-ethyl)-1H-indol-2-yl]-morpholin-4-yl-methanone (intermediate 1, 500 mg, 1.0 eq.), 2-hydroxymethyl-morpholine-4-carboxylic acid tert-butyl ester (purchased at Pharmacore ref 610009, 397 mg, 1.2 eq.) and triphenylphosphine (494 mg, 1.2 eq.) in tetrahydrofuran (10 mL) was slowly added a solution of di-tert-butylazodicarboxylate (429 mg, 1.2 eq.) in tetrahydrofuran (5 mL). The reaction mixture was stirred at room temperature for 72 h, evaporated to dryness in vacuo and purified on silica, eluting with 99:1 dichloromethane/methanol to yield 170 mg (21%) of the desired product as white foam. MS (m/e): 528.5 (MH$^+$, 100%).

Step 2: Morpholin-4-yl-[5-(morpholin-2-ylmethoxy)-1-(2,2,2-trifluoro-ethyl)-1H-indol-2-yl]-methanone as trifluoroacetate salt To a cold mixture (0° C.) of 2-[2-(morpholine-4-carbonyl)-1-(2,2,2-trifluoro-ethyl)-1H-indol-5-yloxymethyl]-morpholine-4-carboxylic acid tert-butyl ester (example 1, step 1, 130 mg, 1.0 eq.) in dichloromethane (2 mL) was added trifluoroacetic acid (0.19 mL, 10 eq.). The reaction mixture was stirred overnight at room temperature and evaporated in vacuo. The residue was mixed with a solution of potassium carbonate (2 g) in water (6 mL) and extracted with ethyl acetate. The combined organic layers were dried over sodium sulfate, filtered and dried in vacuo, to yield 134 mg (100%) of the desired product as white foam. MS (m/e): 428.5 (MH$^+$, 100%).

Step 3: [5-(4-Isopropyl-morpholin-2-ylmethoxy)-1-(2,2,2-trifluoro-ethyl)-1H-indol-2-yl]-morpholin-4-yl-methanone To a solution of morpholin-4-yl-[5-(morpholin-2-ylmethoxy)-1-(2,2,2-trifluoro-ethyl)-1H-indol-2-yl]-methanone as trifluoroacetate salt (example 1, step 2, 120 mg, 1.0 eq.) in tetrahydrofuran (2 mL) were successively added water (0.004 mL, 1.1 eq.), acetone (0.019 mL, 1.5 eq.), acetic acid (0.040 mL, 3.0 eq.) and a solution of sodium cyanoborohydride in tetrahydrofuran (1M, 0.33 mL, 1.5 eq.). The reaction mixture was stirred at 55° C. overnight and concentrated in vacuo. Water (5 mL) and hydrochloric acid (1N, 1.5 mL) were added to the residue and the solution was washed with ethyl acetate and then basified by addition of an aqueous solution of potassium carbonate. The aqueous fraction was extracted with ethyl acetate and the combined organic layers were washed with brine. The organic residue was purified on silica, eluting with 98:2 dichloromethane/methanol, to yield 45 mg (43%) of the desired product as white foam. MS (m/e): 470.5 (MH$^+$, 100%).

Example 2

[5-((R)-1-Isopropyl-piperidin-3-ylmethoxy)-1-(2,2,2-trifluoro-ethyl)-1H-indol-2-yl]-morpholin-4-yl-methanone Step 1: (R)-3-[2-(Morpholine-4-carbonyl)-1-(2,2,2-trifluoro-ethyl)-1H-indol-5-yloxymethyl]-piperidine-1-carboxylic acid tert-butyl ester In analogy to the procedure described for the synthesis of example 1, step 1, the title compound was synthesized from [5-hydroxy-1-(2,2,2-trifluoro-ethyl)-1H-indol-2-yl]-morpholin-4-yl-methanone (intermediate 1) and 3R-hydroxymethyl-piperidine-1-carboxylic acid tert-butyl ester. The title product was obtained in 71% yield as white solid. MS (m/e): 526.5 (MH$^+$, 100%).

The preparation of 3R-hydroxymethyl-piperidine-1-carboxylic acid tert-butyl ester (CAS number 140695-85-8) has already been described (e.g. Bettoni et al, Gaz. Chim. Ital. 1972 102 189).

Step 2: Morpholin-4-yl-[5-((R)-1-piperidin-3-ylmethoxy)-1-(2,2,2-trifluoro-ethyl)-1H-indol-2-yl]-methanone as trifluoroacetate salt.

In analogy to the procedure described for the synthesis of example 1, step 2, the title compound was synthesized from (R)-3-[2-(morpholine-4-carbonyl)-1-(2,2,2-trifluoro-ethyl)-1H-indol-5-yloxymethyl]-piperidine-1-carboxylic acid tert-butyl ester (example 2, step 1). The desired product was obtained in 97% yield as white solid. MS (m/e): 412.5 (MH$^+$, 100%).

Step 3: [5-((R)-1-Isopropyl-piperidin-3-ylmethoxy)-1-(2,2,2-trifluoro-ethyl)-1H-indol-2-yl]-morpholin-4-yl-methanone In analogy to the procedure described for the synthesis of example 1, step 3, the title compound was synthesized from morpholin-4-yl-[5-((R)-1-piperidin-3-ylmethoxy)-1-(2,2,2-trifluoro-ethyl)-1H-indol-2-yl]-methanone as a trifluoroacetic acid salt (Example 2, step 2). The title product was obtained in a 69% yield as white solid. MS (m/e): 468.2 (MH$^+$, 100%).

Example 3

[5-((S)-1-Isopropyl-piperidin-3-ylmethoxy)-1-(2l2,2-trifluoro-ethyl)-1H-indol-2-yl]-morpholin-4-yl-methanone Step 1: (S)-3-[2-(Morpholine-4-carbonyl)-1-(2,2,2-trifluoro-ethyl)-1H-indol-5-yloxymethyl]-piperidine-1-carboxylic acid tert-butyl ester In analogy to the procedure described for the synthesis of example 1, step 1, the title compound was synthesized from [5-hydroxy-1-(2,2,2-trifluoro-ethyl)-1H-indol-2-yl]-morpholin-4-yl-methanone (intermediate 1) and 3S-hydroxymethyl-piperidine-1-carboxylic acid tert-butyl ester. The desired compound was obtained in 69% yield as white solid. MS (m/e): 526.5 (MH$^+$, 100%).

The preparation of 3S-hydroxymethyl-piperidine-1-carboxylic acid tert-butyl ester (CAS number 140695-84-7) has already been described (e.g. Bettoni et al, Gaz. Chim. Ital. 1972, 102 189).

Step 2: Morpholin-4-yl-[5-((S)-1-piperidin-3-ylmethoxy)-1-(2,2,2-trifluoro-ethyl)-1H-indol-2-yl]-methanone trifluoroacetate salt In analogy to the procedure described for the synthesis of example 1, step 2, the title compound was synthesized from (S)-3-[2-(morpholine-4-carbonyl)-1-(2,2,2-trifluoro-ethyl)-1H-indol-5-yloxymethyl]-piperidine-1-carboxylic acid tert-butyl ester (example 3, step 1). The desired compound was obtained in 99% yield as white solid. MS (m/e): 412.5 (MH$^+$, 100%).

Step 3: [5-((S)-1-Isopropyl-piperidin-3-ylmethoxy)-1-(2,2,2-trifluoro-ethyl)-1H-indol-2-yl]-morpholin-4-yl-methanone In analogy to the procedure described for the synthesis of example 1, step 3, the title compound was synthesized from morpholin-4-yl-[5-((S)-1-piperidin-3-ylmethoxy)-1-(2,2,2-trifluoro-ethyl)-1H-indol-2-yl]-methanone trifluoroacetate salt (example 3, step 2). The title compound was obtained in 19% yield as white solid. MS (m/e): 468.2 (MH$^+$, 100%).

Example 4

{5-[3-(2-Aza-bicyclo[3.1.0]hex-2-yl)-propoxy]-1H-indol-2-yl}-morpholin-4-yl-methanone Step 1: 5-(3-Chloro-propoxy)-1H-indole-2-carboxylic acid ethyl ester A mixture of ethyl-5-hydroxyindole-2-carboxylate (purchased at Biosynth, Ref H-6350, 15 g, 1.0 eq.), 1-bromo-3-chloropropane (8.8 mL, 1.2 eq.) and potassium carbonate (12.12 g, 1.2 eq.) in butanone (200 mL) was stirred 4 days at reflux. The reaction mixture was partitioned between ethyl acetate and water. The aqueous layer was extracted with ethyl acetate. The combined organic layers were washed with water and brine, evaporated in vacuo and purified on silica, eluting with a 19:1 to 2:1 gradient of cyclohexane/ethyl acetate to yield 15.3 g (74%) of the desired product as light yellow solid. MS (m/e): 282.5 (MH$^+$, 100%).

Step 2: 5-(3-Chloro-propoxy)-1H-indole-2-carboxylic acid

In analogy to the procedure described for the synthesis of intermediate 1, step 3, the title compound was synthesized from 5-(3-chloro-propoxy)-1H-indole-2-carboxylic acid ethyl ester (example 4, step 1). The title compound was obtained in 98% yield as white solid. MS (m/e): 252.9 (M−H$^-$, 100%).

Step 3: [5-(3-Chloro-propoxy)-1H-indol-2-yl]-morpholin-4-yl-methanone

In analogy to the procedure described for the synthesis of intermediate 1, step 4, the title compound was synthesized from 5-(3-chloro-propoxy)-1H-indole-2-carboxylic acid (Example 4, step 2) and morpholine. The desired product was obtained as white solid in 84% yield. MS (m/e): 324.0 (MH$^+$, 100%).

Step 4: 2-Methoxy-pyrrolidine-1-carboxylic acid benzyl ester

To a mixture of (S)-pyrrolidine-1,2-dicarboxylic acid 1-benzyl ester (purchased at Fluka, Ref 97090, 6 g, 1.0 eq.) in dichloromethane (300 mL) was added diacetoxyiodosobenzene (15.8 g, 2 eq.) and iodine (3.0 eq., 0.5 eq.). The mixture was stirred 5 h at room temperature. Methanol (12 mL) was added and the reaction mixture was stirred for an additional 1.5 h at room temperature, partitioned between an aqueous solution of sodium sulfite and dichloromethane. The organic layer was washed with an aqueous solution of sodium sulfite, brine, evaporated in vacuo and purified on silica eluting with 9:1 cyclohexane/ethyl acetate to yield 5.0 g (88%) of the desired product as light yellow oil. MS (m/e): 235.5 (MH$^+$, 100%)

Step 5: 2,3-Dihydro-pyrrole-1-carboxylic acid benzyl ester

To a cold (0° C.) solution of 2-methoxy-pyrrolidine-1-carboxylic acid benzyl ester (example 4, step 4, 500 mg, 1.0 eq.) in dichloromethane was added N-diisopropylethyl-amine (0.5 mL, 1.36 eq.) and trimethylsilyltrifluoromethanesulfonate (0.51 mL, 1.3 eq.). The reaction mixture was stirred at 0° C. for 30 min and partitioned between dichloromethane and an aqueous solution of sodium hydrogencarbonate. The aqueous layer was extracted with dichloromethane. The combined organic layers were washed with water and evaporated in vacuo and purified on silica eluting with 19:1 cyclohexane/ethyl acetate to yield 325 mg (75%) of the desired product as a colourless oil. MS (m/e): 204.5 (MH$^+$, 100%).

Step 6: 2-Aza-bicyclo[3.1.0]hexane-2-carboxylic acid benzyl ester

To a cold (0° C.) solution of 2,3-dihydro-pyrrole-1-carboxylic acid benzyl ester (example 4, step 5, 300 mg, 1.0 eq.) in diethyl ether was slowly added a solution of diethylzinc in hexanes (1M, 7 mL, 4.75 eq.), followed by chloroiodomethane (1.1 mL, 10 eq.). The reaction mixture was stirred 3 h at 0° C., allowed to warm up to room temperature and stirred an additional 3 h. The reaction mixture was partitioned between an aqueous solution of ammonium chloride and diethyl ether. The aqueous layer was extracted with diethyl ether and the combined organic layers were washed with brine, dried over sodium sulphate and evaporated in vacuo and purified on silica, eluting with a 1:1 to 1:3 gradient of cyclohexane/dichloromethane, to yield 160 mg (50%) of the desired product as colourless oil. MS (m/e): 218.5 (MH$^+$, 100%)

Step 7: 2-Aza-bicyclo[3.1.0]hexane hydrochloride.

A mixture of 2-aza-bicyclo[3.1.0]hexane-2-carboxylic acid benzyl ester (example 4, step 6, 130 mg, 1.0 eq.) and palladium on activated charcoal (10% in mass, 64 mg, 0.1 eq.), in a solution of hydrochloric acid in ethyl acetate (2.23M, 1 mL) and ethanol (10 mL) was vigorously stirred 24 h at room temperature under an atmosphere of hydrogen (1 Atm). The reaction mixture was filtered on a dicalite pad and the pad was washed with ethanol. The filtrate was evaporated in vacuo and purified by precipitation with dichloromethane/tert-butyl-methylether to yield 69 mg (96%) of the desired product as brown solid. MS (m/e): 82 (M–H$^-$, 100%).

Step 8: {5-[3-(2-Aza-bicyclo[3.1.0]hex-2-yl)-propoxy]-1H-indol-2-yl}-morpholin-4-yl-methanone A mixture of 2-aza-bicyclo[3.1.0]hexane hydrochloride (example 4 step 7, 49 mg, 1.2 eq.) and potassium carbonate (118 mg, 2.5 eq.) in acetonitrile was stirred 1 h at 60° C. The reaction mixture was cooled to 30° C. and [5-(3-chloro-propoxy)-1H-indol-2-yl]-morpholin-4-yl-methanone (example 4, step 3, 110 mg, 1.0 eq.) was added. The resulting mixture was stirred 24 h at 80° C. The reaction mixture was partitioned between ethyl acetate and water. The aqueous layer was extracted with ethyl acetate and the combined organic layers were washed with an aqueous solution of sodium hydrogencarbonate and water and dried over sodium sulphate and evaporated in vacuo. The residue was purified on silica, eluting with a 98:2 to 9:1 gradient of dichloromethane/methanol, to yield 12 mg (8%) of the desired product as light yellow solid. MS (m/e): 370.4 (MH$^+$, 100%).

Example 5

{5-[3-(3-Aza-bicyclo[3.1.0]hex-3-yl)-propoxy]-1H-indol-2-yl}-morpholin-4-yl-methanone Step 1: 3-(3-Hydroxy-propyl)-3-aza-bicyclo[3.1.0]hexane-2,4-dione A mixture of cyclopropane-2,3-dicarboxylic acid anhydride (purchased at Acros, Ref 37012-0010, 500 mg, 1.0 eq.) and 3-amino-1-propanol (340 mL, 1.0 eq.) was heated 6 h at 180° C. The reaction mixture was purified on silica, eluting with a 98:2 to 19:1 gradient of dichloromethane/methanol, to yield 360 mg (49%) of the desired product as light yellow solid. MS (m/e): 168.1 (M–H$^-$, 100%)

Step 2: 3-(3-Aza-bicyclo[3.1.0]hex-3-yl)-propan-1-ol

To a cold (0° C.) solution of sodium dihydro-bis(2-methoxyethoxy)aluminate in toluene (70% in mass, 2.43 mL, 4.5 eq.) was added 3-(3-hydroxy-propyl)-3-azabicyclo[3.1.0]hexane-2,4-dione (example 5, step 1, 320 mg, 1.0 eq.) in diethyl ether (5 mL). The mixture was stirred 40 min at 0° C. and 4 h at reflux. Water was carefully added to and the white mixture was filtered on a dicalite pad. The filtrate was extracted with diethyl ether and the combined organic layers were dried over sodium sulfate, filtered and evaporated in vacuo, yielding 220 mg (78%) of the desired product as a purple liquid which was used without additional purification. MS (m/e): 143.1 (MH$^+$, 100%).

Step 3: (5-Hydroxy-1H-indol-2-yl)-morpholin-4-yl-methanone

In analogy to the procedure described for the synthesis of intermediate 1, step 4, the title compound was synthesized from 5-hydroxy-1H-indole-2-carboxylic acid (purchased at Fluka, Ref 55355) and morpholine. The desired product was obtained in 86% yield as white solid. MS (m/e): 493.1 (2M$^+$, 100%).

Step 4: {5-[3-(3-Aza-bicyclo[3.1.0]hex-3-yl)-propoxy]-1H-indol-2-yl}-morpholin-4-yl-methanone In analogy to the procedure described for the synthesis of example 1, step 1, the title compound was synthesized from (5-hydroxy-1H-indol-2-yl)-morpholin-4-yl-methanone (example 5, step 3) and 3-(3-aza-bicyclo[3.1.0]hex-3-yl)-propan-1-ol (example 5, step 2). The title product was obtained in 49% yield as white solid. MS (m/e): 370.5 (MH$^+$, 100%).

Example 6

[5-[3-(3-Aza-bicyclo[3.1.0]hex-3-yl)-propoxy]-1-(2,2,2-trifluoro-ethyl)-1H-indol-2-yl]-morpholin-4-yl-methanone In analogy to the procedure described for the synthesis of intermediate 1, step 1, the title compound was synthesized from {5-[3-(3-aza-bicyclo[3.1.0]hex-3-yl)-propoxy]-1H-indol-2-yl}-morpholin-4-yl-methanone (Example 5, step 4) and 2,2,2-trifluoroethyl-trifluoromethanesulfonate. The title product was obtained in 45% yield as white solid. MS (m/e): 452.5 (MH$^+$, 100%).

Example 7

3-endo-[5-(8-Isopropyl-8-aza-bicyclo[3.2.1]oct-3-yloxy)-1-(2,2,2-trifluoro-ethyl)-1H-indol-2-yl]-morpholin-4-yl-methanone Step 1: 3-endo-3-Hydroxy-8-aza-bicyclo[3.2.1]octane-8-carboxylic acid tert-butyl ester To a stirred suspension of nortropine (1.272 g, 1 eq.) in tetrahydrofuran (25 mL) was added di-tert-butyl-dicarbonate (2.292 g, 1.05 eq.). The mixture was stirred overnight at room temperature. The solvent was evaporated under reduced pressure and the residue purified by column chromatography on silica gel eluting with a 1:0 to 4:1 gradient of dichloromethane/ethyl acetate, to yield 2.207 g (97%) of the title compound as colourless solid. MS (m/e) 227.2 (M$^+$)

Step 2: 3-exo-3-(4-Nitro-benzoyloxy)-8-aza-bicyclo[3.2.1]octane-8-carboxylic acid tert-butyl ester To a solution of 3-endo-3-hydroxy-8-aza-bicyclo[3.2.1]octane-8-carboxylic acid tert-butyl ester (227 mg, 1.0 eq.), triphenylphosphine (393 mg, 1.5 eq.) and 4-nitrobenzoic acid (250 mg, 1.5 eq.) in tetrahydrofuran (4 mL) was added diethylazodicarboxylate (0.23 mL, 1.5 eq.) dropwise. The mixture was stirred overnight at room temperature. The mixture was poured into water (20 mL) and the organics extracted with ethyl acetate. The combined organic phases were washed with brine, dried over magnesium sulfate and evaporated under reduced pressure to afford an oil that was purified by column chromatography on silica gel eluting with 4:1 heptane/ethyl acetate to yield 340 mg (90%) of the title product as white solid. MS (m/e) 377.4 (M+H)$^+$.

Step 3: 3-exo-3-Hydroxy-8-aza-bicyclo[3.2.1]octane-8-carboxylic acid tert-butyl ester To a solution of 3-exo-3-(4-nitro-benzoyloxy)-8-aza-bicyclo[3.2.1]octane-8-carboxylic acid tert-butyl ester (575 mg, 1.0 eq.) in tetrahydrofuran was added a solution of lithium hydroxide hydrate (77 mg, 1.2 eq.) in water (1 mL). The heterogeneous mixture was stirred overnight at room temperature and poured into aqueous potassium dihydrogen phosphate (1M). The organics were extracted with ethyl acetate, the combined organic phases washed with brine, dried over magnesium sulfate and evaporated under reduced pressure. The solid residue was purified by column chromatography on silica gel eluting with 4:1 ethyl acetate/heptane eluant to yield 345 mg (99%) of the title product as white solid. MS (m/e) 227.2 (M$^+$)

Step 4: 3-endo-3-[2-(Morpholine-4-carbonyl)-1-(2,2,2-trifluoro-ethyl)-1H-indol-5-yloxy]-8-aza-bicyclo[3.2.1]octane-8-carboxylic acid tert-butyl ester To a cooled (ice-bath) mixture of [5-hydroxy-1-(2,2,2-trifluoro-ethyl)-1H-indol-2-yl]-morpholin-4-yl-methanone (intermediate 1, step 4, 200 mg, 1.0 eq.), 3-exo-3-hydroxy-8-aza-bicyclo[3.2.1]octane-8-carboxylic acid tert-butyl ester (166 mg, 1.2 eq.) and triphenylphosphine (200 mg, 1.25 eq.) in tetrahydrofuran (5 mL) was added a solution of diethylazodicarboxylate in tetrahydrofuran (1 mL) dropwise. The yellow mixture was stirred 1 week at room temperature. The mixture was evaporated under reduced pressure and the residue purified by column chromatography on silica gel eluting with 19:1 chloroform/tert-butylmethyl ether to yield 212 mg (64%) of the title product as pale yellow foam. MS (m/e) 538.5 (M+H)$^+$.

Step 5: 3-endo-[5-(8-Isopropyl-8-aza-bicyclo[3.2.1]oct-3-yloxy)-1-(2,2,2-trifluoro-ethyl)-1H-indol-2-yl]-morpholin-4-yl-methanone To a cooled (ice-bath) solution of 3-[2-(morpholine-4-carbonyl)-1-(2,2,2-trifluoro-ethyl)-1H-indol-5-yloxy]-8-aza-bicyclo[3.2.1]octane-8-carboxylic acid tert-butyl ester (example 7, step 4) in ethyl acetate (4 mL) and isopropanol (4 mL) was added a solution of hydrochloric acid in ethyl acetate (2.23M, 1 mL) dropwise. The mixture was kept 48 h at room temperature. The mixture was evaporated to dryness under reduced pressure to afford the hydrochloric salt of the deprotected amine as a white solid. The solid was suspended in 1,2-dichloroethane and triethylamine added dropwise. The solid dissolved, acetone was added, followed by sodium triacetoxyborohydride. The mixture was stirred 72 h at room temperature. The reaction was quenched by adding saturated aqueous sodium bicarbonate solution and the product extracted with ethyl acetate. The combined organic phases were dried over magnesium sulfate and evaporated under reduced pressure. The crude product was purified by column chromatography on silica gel eluting with a gradient of chloroforme/methanol/ammoniac to yield the title product as off-white solid. MS (m/e) 480.5 (M+H)$^+$

Example 8

3-endo-(4,4-Difluoro-piperidin-1-yl)-[5-(8-isopropyl-8-aza-bicyclo[3.2.1]oct-3-yloxy)-1-(2,2,2-trifluoro-ethyl)-1H-indol-2-yl]-methanone Step 1: (4,4-Difluoro-piperidin-1-yl)-[5-hydroxy-1-(2,2,2-trifluoro-ethyl)-1H-indol-2-yl]-methanone In analogy to the procedure described for the synthesis of intermediate 1, step 4, the title compound was synthesized from 5-hydroxy-1-(2,2,2-trifluoro-ethyl)-1H-indole-2-carboxylic acid (Intermediate 1, step 3) and 4,4-difluoropiperidine hydrochloride. The title product was obtained in 80% as white solid. MS (m/e): 361 (M–H$^-$, 100%).

Step 2: 3-endo-3-[2-(4,4-Difluoro-piperidine-1-carbonyl)-1-(2,2,2-trifluoro-ethyl)-1H-indol-5-yloxy]-8-aza-bicyclo[3.2.1]octane-8-carboxylic acid tert-butyl ester In analogy to the procedure described for the synthesis of example 7, step 4, the title compound was synthesized from (4,4-difluoro-piperidin-1-yl)-[5-hydroxy-1-(2,2,2-trifluoro-ethyl)-1H-indol-2-yl]-methanone (example 8, step 1) and 3-exo-3-hydroxy-8-aza-bicyclo[3.2.1]octane-8-carboxylic acid tert-butyl ester. The title product was obtained in a yield of 75% as pale yellow foam. MS (m/e) 572.5 (M+H)$^+$.

Step 3: 3-endo-(4,4-Difluoro-piperidin-1-yl)-[5-(8-isopropyl-8-aza-bicyclo[3.2.1]oct-3-yloxy)-1-(2,2,2-trifluoro-ethyl)-1H-indol-2-yl]-methanone In analogy to the procedure described for the synthesis of example 7, step 5, the title compound was synthesized from 3-endo-3-[2-(4,4-difluoro-piperidine-1-carbonyl)-1-(2,2,2-trifluoro-ethyl)-1H-indol-5-yloxy]-8-aza-bicyclo[3.2.1]octane-8-carboxylic acid tert-butyl ester (example 8, step 2). Off-white solid. MS (m/e) 514.5 (M+H)$^+$.

Example 9

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example 10

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 11

Injection solutions can have the following composition:

| | |
|---|---|
| Compound of formula (I) | 3.0 mg |
| Gelatin | 150.0 mg |
| Phenol | 4.7 mg |
| Sodium carbonate | to obtain a final pH of 7 |
| Water for injection solutions | ad 1.0 ml |

Example 12

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide (yellow) | 1.1 mg |

The active ingredient is dissolved in a warm melt of the other ingredients and the mixture is filled into soft gelatin capsules of appropriate size. The filled soft gelatin capsules are treated according to the usual procedures.

Example 13

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

It is to be understood that the invention is not limited to the particular embodiments of the invention described above, as variations of the particular embodiments may be made and still fall within the scope of the appended claims.

What is claimed is:

1. A compound of formula (I):

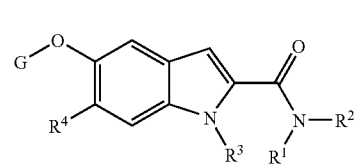

or a pharmaceutically acceptable salt thereof, wherein:
$R^1$ and $R^2$ together with the nitrogen atom to which they are attached form a 6-membered saturated or partly unsaturated heterocyclic ring optionally containing a further heteroatom or group selected from the group consisting of nitrogen, oxygen, sulphur, a sulfinyl group, and a sulfonyl group, wherein said heterocyclic ring is unsubstituted or substituted by one, two or three substituents independently selected from the group consisting of (1) lower alkyl, (2) halogen, (3) halogenoalkyl, (4) hydroxy, (5) lower hydroxyalkyl, (6) lower alkoxy, (7) oxo, (8) phenyl, (9) benzyl, (10) pyridyl and (11) carbamoyl, and wherein said heterocyclic ring is optionally condensed with a phenyl ring wherein said phenyl ring is unsubstituted or substituted by one, two or three substituents independently selected from the group consisting of lower alkyl, lower alkoxy and halogen;
$R^3$ is selected from the group consisting of (1) hydrogen, (2) lower alkyl, (3) lower hydroxyalkyl, (4) lower alkoxyalkyl, (5) lower halogenoalkyl, (6) lower cycloalkylalkyl, (7) lower alkanoyl, (8) lower cyanoalkyl, (9) lower alkylsulfonyl, (10) phenylsulfonyl wherein the phenyl ring is unsubstituted or substituted with one or two substituents independently selected from the group consisting of lower alkyl, halogen, lower alkoxy lower halogenoalkoxy and lower hydroxyalkyl; (11) phenyl unsubstituted or substituted with one or two substituents independently selected from the group consisting of lower alkyl, halogen, lower alkoxy, lower halogenoalkoxy and lower hydroxyalkyl; and (12) lower phenylalkyl, wherein the phenyl ring is unsubstituted or substituted with one or two substituents independently selected from the group consisting of lower alkyl, halogen, lower alkoxy, lower halogenoalkoxy and lower hydroxyalkyl;
$R^4$ hydrogen or halogen;
G is selected from the group consisting of:

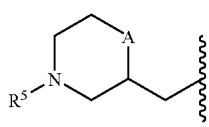

G1

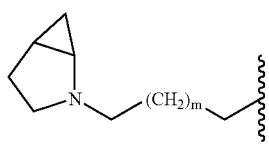

G2

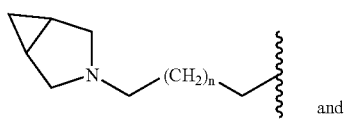

G3

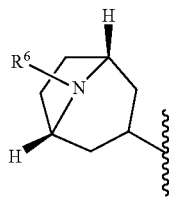

G4 wherein:
$R^5$ is lower alkyl, cycloalkyl, lower cycloalkylalkyl, or lower phenylalkyl;
A is $CH_2$, O or S;
m is 0, 1 or 2;
n is 0, 1 or 2; and
$R^6$ is lower alkyl or cycloalkyl.

2. A compound according to claim 1, wherein $R^1$ and $R^2$ together with the nitrogen atom to which they are attached form a heterocyclic ring selected from the group consisting of morpholine, piperidine, piperazine, thiomorpholine, 1-oxo-thiomorpholine, 1,1-dioxothiomorpholine and 3,6-dihydro-2H-pyridine, wherein said heterocyclic ring is unsubstituted or substituted by one, two or three substituents independently selected from the group consisting of(1) lower alkyl, (2) halogen, (3) halogenoalkyl, (4) hydroxy, (5) lower alkoxy, (6) oxo, (8) phenyl, (9) benzyl, (10) pyridyl and (11) carbamoyl, and wherein said heterocyclic ring is optionally condensed with a phenyl ring, wherein said phenyl ring is unsubstituted or substituted by one, two or three substituents independently selected from the group consisting of lower alkyl, lower alkoxy and halogen.

3. A compound according to claim 1, wherein $R^1$ and $R^2$ together with the nitrogen atom to which they are attached form a heterocyclic ring selected from the group consisting of morpholine, piperidine, and 4,4-difluoropiperidine.

4. A compound according to claim 1, wherein $R^3$ is selected from the group consisting of: (1) hydrogen, (2) lower alkyl, (3) lower hydroxyalkyl, (4) lower alkoxyalkyl, (5) lower halogenoalkyl, (6) lower cycloalkylalkyl, (7) lower cyanoalkyl, (8) lower alkylsulfonyl, and (9) phenyl unsubstituted or substituted with one or two substituents independently selected from the group consisting of lower alkyl, halogen, lower alkoxy, lower halogenoalkoxy and lower hydroxyalkyl.

5. A compound according to claim 1, wherein $R^3$ is selected from the group consisting of hydrogen, lower alkyl and lower halogenoalkyl.

6. A compound according to claim 1, wherein $R^3$ is lower halogenoalkyl.

7. A compound according to claim 1, wherein $R^4$ is hydrogen.

8. A compound according to claim 1, wherein G is:

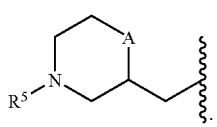

G1

9. A compound according to claim 1, wherein A is O.
10. A compound according to claim 1, wherein A is $CH_2$.
11. A compound according to claim 1, wherein G is:

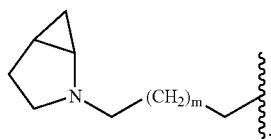

G2

12. A compound according to claim 1, wherein G is:

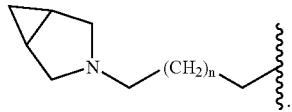

G3

13. A compound according to claim 1, wherein G is:

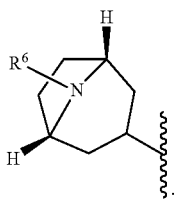

14. A compound according to claim 1, wherein $R^6$ is lower alkyl.

15. A compound according to claim 1, selected from the group consisting of:
- [5-(4-isopropyl-morpholin-2-ylmethoxy)-1-(2,2,2-trifluoro-ethyl)-1H-indol-2-yl]-morpholin -4-yl-methanone,
- [5-((R)-1-isopropyl-piperidin-3-ylmethoxy)-1-(2,2,2-trifluoro-ethyl)-1H-indol-2-yl]-morpholin -4-yl-methanone, and any pharmaceutically acceptable salt thereof.

16. A compound according to claim 1, selected from the group consisting of:
- [5-((S)-1-isopropyl-piperidin-3-ylmethoxy)-1-(2,2,2-trifluoro-ethyl)-1H-indol-2-yl]-morpholin -4-yl-methanone,
- {5-[3-(2-aza-bicyclo[3.1.0 ]hex-2-yl)-propoxy]-1H-indol-2-yl }-morpholin-4-yl -methanone, and any pharmaceutically acceptable salt thereof.

17. A compound according to claim 1, selected from the group consisting of:
- {5-[3-(3-aza-bicyclo[3.1.0]hex-3-yl)-propoxy]-1H-indol-2-yl }-morpholin-4-yl -methanone,
- [5-[3-(3-aza-bicyclo[3.1.0]hex-3-yl)-propoxy]-1-(2, 2,2-trifluoro-ethyl)-1H-indol-2-yl]-morpholin-4-yl-methanone, and any pharmaceutically acceptable salt thereof.

18. A compound according to claim 1, selected from the group consisting of:
- 3-endo-5-(8-isopropyl-8-aza-bicyclo[3 .2.1 ]oct-3-yloxy)-1-(2,2,2-trifluoro-ethyl)-1 indol-2-yl]-morpholin-4-yl-methanone, 3-endo-(4,4-difluoro-piperidin-1-yl)-[5-(8-isopropyl-8-aza-bicyclo[3.2.1]oct-3-yloxy)-1-(2,2,2-trifluoro-ethyl)-1H-indol-2-yl]-methanone, and any pharmaceutically acceptable salt thereof.

19. A pharmaceutical composition, comprising a therapeutically effective amount of a compound according to claim 1 as well as a pharmaceutically acceptable carrier and/or adjuvant.

* * * * *

UNITED STATES PATENT AND TRADEMARK OFFICE
CERTIFICATE OF CORRECTION

PATENT NO. : 7,388,095 B2
APPLICATION NO. : 11/604563
DATED : June 17, 2008
INVENTOR(S) : Matthias Nettekoven et al.

Page 1 of 1

It is certified that error appears in the above-identified patent and that said Letters Patent is hereby corrected as shown below:

Column 44, claim 18, line 16, delete "-1-(2,2,2-trifluoro-ethyl)-1 indol-2-yl]-morpholin-4-yl-" and insert
-- -1-(2,2,2-trifluoro-ethyl)-1H-indol-2-yl]-morpholin-4-yl- --.

Signed and Sealed this

Twenty-third Day of June, 2009

JOHN DOLL
*Acting Director of the United States Patent and Trademark Office*